US010274467B2

(12) United States Patent
Kim et al.

(10) Patent No.: US 10,274,467 B2
(45) Date of Patent: Apr. 30, 2019

(54) GAS SENSOR AND MEMBER USING METAL OXIDE SEMICONDUCTOR NANOFIBERS INCLUDING NANOPARTICLE CATALYST FUNCTIONALIZED BY BIFUNCTIONAL NANO-CATALYST INCLUDED WITHIN APOFERRITIN, AND MANUFACTURING METHOD THEREOF

(71) Applicant: Korea Advanced Institute of Science and Technology, Daejeon (KR)

(72) Inventors: Ii-Doo Kim, Seoul (KR); Sang-Joon Kim, Daejeon (KR); Seon-Jin Choi, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 57 days.

(21) Appl. No.: 14/855,975

(22) Filed: Sep. 16, 2015

(65) Prior Publication Data

US 2016/0077069 A1    Mar. 17, 2016

(30) Foreign Application Priority Data

Sep. 17, 2014    (KR) .......................... 10-2014-0123563

(51) Int. Cl.
*G01N 31/10*    (2006.01)
*D01D 5/00*    (2006.01)
(Continued)

(52) U.S. Cl.
CPC .............. *G01N 31/10* (2013.01); *B82Y 30/00* (2013.01); *C04B 35/62227* (2013.01); *D01D 5/0038* (2013.01); *D01F 9/10* (2013.01)

(58) Field of Classification Search
CPC ... B01J 23/63; B01J 23/40; B01J 23/80; B01J 23/78; B01J 23/755; B01J 23/48;
(Continued)

(56) References Cited

U.S. PATENT DOCUMENTS 8,535,632 B2 *    9/2013    Chase ................ B01D 53/8678
422/139

OTHER PUBLICATIONS

Huheey et al., "Inorganic Chemistry, Principles of Structure of Reactivity," Fourth Edition, pp. 272-275, 1993.

* cited by examiner

*Primary Examiner* — James A Fiorito
(74) *Attorney, Agent, or Firm* — Blank Rome LLP

(57) ABSTRACT

The inventive concepts relate to a member for a gas sensor, a gas sensor using the same and a manufacturing method thereof, and more particularly, to a member for a gas sensor using a one-dimensional metal oxide nanofiber complex material containing hetero nanoparticle catalysts synthesized using apo-ferritins, a gas sensor using the same, and a manufacturing method thereof.

According to embodiments of the inventive concepts, apo-ferritins containing hetero nanoparticle catalysts are mixed with an electrospinning solution, the mixture solution is electrospun to form complex nanofibers, and then a high-temperature thermal treatment process is performed to remove the apo-ferritins. Thus, the hetero nanoparticle catalysts are uniformly fastened to an inside and a surface of one-dimensional metal oxide nanofibers to form a member for a gas sensor. As a result, the member for a gas sensor has a high-sensitivity characteristic capable of sensing a very small amount of a gas and excellent selectivity capable of sensing various gases. In addition, a catalyst effect is maximized by the hetero nanoparticle catalysts uniformly distributed without aggregation. Furthermore, the member for (Continued)

a gas sensor and the gas sensor using the same can be mass-produced by a process method capable of effectively forming pores and of fastening high-performance catalysts.

15 Claims, 22 Drawing Sheets
(15 of 22 Drawing Sheet(s) Filed in Color)

(51) Int. Cl.
*D01F 9/10* (2006.01)
*B82Y 30/00* (2011.01)
*C04B 35/622* (2006.01)

(58) Field of Classification Search
CPC . B01J 23/60; B01J 23/62; B01J 23/652; B01J 23/68; B01J 23/682; B01J 23/64; B01J 23/648; G01N 31/10; B82Y 30/00; C04B 35/62227; D01D 5/0038; D01F 9/10
USPC ....... 502/325, 326, 329, 330, 332, 333–335, 502/339
See application file for complete search history.

GAS SENSOR AND MEMBER USING METAL OXIDE SEMICONDUCTOR NANOFIBERS INCLUDING NANOPARTICLE CATALYST FUNCTIONALIZED BY BIFUNCTIONAL NANO-CATALYST INCLUDED WITHIN APOFERRITIN, AND MANUFACTURING METHOD THEREOF

CROSS-REFERENCE TO RELATED APPLICATION

This U.S. non-provisional patent application claims priority under 35 U.S.C. § 119 to Korean Patent Application No. 10-2014-0123563, filed on Sep. 17, 2014, in the Korean Intellectual Property Office, the disclosure of which is hereby incorporated by reference in its entirety.

BACKGROUND

The inventive concepts relate to a member for a gas sensor, a gas sensor using the same, and a manufacturing method thereof. More particularly, the inventive concepts relate to a nanoparticle catalyst-metal oxide nanofiber complex obtained by synthesizing an alloy nanoparticle within an apo-ferritin protein shell and functionalizing the alloy nanoparticle in the inside and on a surface of metal oxide semiconductor nanofibers, a member for a gas sensor using the same, a gas sensor using the same, and a manufacturing method thereof.

A metal oxide semiconductor-based gas sensors use a phenomenon that an electrical resistance value is varied by surface reaction occurring in a process of adsorbing and desorbing a specific kind of gas molecules on and from the surface of metal oxide semiconductor sensing materials.

The metal oxide semiconductor-based resistance variable gas sensors use a principle that a concentration of a gas is quantitatively detected by analyzing a ratio ($R_{gas}/R_{air}$) of a resistance ($R_{gas}$) in the specific gas to a resistance ($R_{air}$) in air, so constituents of a sensor system may be simplified and a size of the sensor system may be reduced. In addition, since various kinds of sensor arrays are manufactured at relatively low costs, the resistance variable gas sensors are widely used in various fields such as a harmful gas leak alarm, an air pollution measuring instrument, an alcohol detector, and a fire alarm.

Recently, various researches have been conducted for an exhaled breath sensor that accurately detects a very small amount of a biomarker in exhaled breath to early diagnosis of a specific disease in the human body. Specific metabolites are occurred during metabolism of disease factors in the body. These metabolites may be used as a biomarker representing the specific disease. Most of these metabolites may be in a volatile organic compound gas state, so a very small amount of these materials may be exhausted by the exhaled breath through the lungs. Acetone ($CH_3COCH_3$), toluene ($C_6H_5CH_3$), ammonia ($NH_3$), nitrogen monoxide (NO), and hydrogen sulfide ($H_2S$) correspond to representative biomarkers in the exhaled breath and are known as gases related to diabetes, lung disease, kidney disease, asthma, and foul breath, respectively.

As awareness of a health issue becomes higher, there is requirement of a sensor technique capable of rapidly detecting of a very low concentration of harmful environmental gases to the human body or a high-sensitivity, high-selectivity and high-response sensor technique capable of early monitoring whether the human body is abnormal or not. Conventional metal oxide semiconductor-based gas sensors may have a long response time and a long recovery time of several seconds to several minutes. The response time may be a time for which the gas sensor responds to the gas, and the recovery time may be a time for which the gas sensor returns to the original condition. In addition, a performance of the conventional metal oxide semiconductor-based gas sensors may be rapidly varied according to humidity, pressure, temperature and atmosphere of the circumference. Furthermore, the conventional metal oxide semiconductor-based gas sensors may have poor selectivity with respect to a specific gas and may not have a limit of detection which is capable of measuring a gas having a very low concentration of several ppb (part per billion) to hundreds ppb. Thus, a sensing material for a super-sensitivity gas sensor should be developed to accurately detect a very small amount of gases included the exhaled breath of the human body using the metal oxide semiconductor-based gas sensors.

To manufacture a super-sensitivity metal oxide semiconductor-based gas sensor, various researches are conducted for synthesis of various nanostructure-based sensing materials including nanoparticles, nanowires and nanotubes and sensors using the same. Since these nanostructures have large surface areas responding to gases, gas sensing characteristics of the nanostructures may be increased. In addition, since the nanostructures have porous structures, the gases may be rapidly diffused into the sensing material to allow the gas sensor to respond to the gases at a very high speed.

In addition to the researches which synthesize the nanostructures to increase a specific surface and a porosity of the sensing materials, researches are also conducted for a method of developing a super-sensitivity sensing material by fastening metal or metal oxide catalyst particles to a sensing member in order to detect a very small amount (e.g., tens ppb) of a gas. In the case that the catalyst is used, selectivity and a sensing characteristic of the gas sensor may be improved by a chemical sensitization method increasing a concentration of adsorption ions (e.g., $O^-$, $O^2$ and $O_2^-$) using a metal catalyst (e.g., platinum (Pt) or gold (Au)), or an electronic sensitization method improving sensitivity based on an oxidation number variation of palladium (Pd) or silver (Ag) (e.g., an oxidation number variation generated during formation of PdO or $Ag_2O$).

However, even though researches are continuously conducted for the super-sensitivity sensing materials using the nanostructure having the large specific surface and many pores and several kinds of nanoparticle catalyst, the gas sensor may not have a characteristic capable of accurately detecting the gas having a low concentration of hundreds ppb or less with a high response speed and a high recovery speed.

In method of synthesizing the sensing materials, a process of manufacturing the nanostructure and a process of forming the pores may be complicated and difficult. When the nanostructure is synthesized using a deposition method or a chemical growth method, the nanostructure may be formed through complex processes to cause high manufacture costs and difficulties of mass production.

In addition, it may be difficult to manufacture the metal or metal oxide catalyst having a size of several nanometers and to uniformly distribute the catalyst on an entire area of the sensing material. For example, if the metal catalyst is synthesized using a polyol process, catalyst particles may have relatively large sizes (e.g., 3 nm to 10 nm) and may easily aggregate to each other. Thus, it may be difficult to uniformly distribute the catalyst particles on the surface of the metal oxide semiconductor sensing materials.

New materials and processes should be developed to overcome the problems described above. For example, it may be required to develop a simple process capable of manufacturing the nanostructure. In addition, it may be required to develop functional nano catalysts capable of being uniformly distributed without aggregation during a high-temperature thermal treatment process necessary to synthesize the sensing materials. Moreover, it may be required to develop a process of uniformly fastening the functional nano catalysts to the sensing materials having the nanostructure. Furthermore, it may be required to develop a method of easily synthesizing, in bulk, a new super-sensitivity sensing material that overcomes limitations of conventional noble metal-based catalysts to maximize catalyst activation. It may also be required to apply the new super-sensitivity sensing material to a sensor that accurately and selectively detects a harmful environmental gas and various kinds of volatile organic compounds included in the exhaled breath. In particular, it is required to develop a new catalyst synthesis process method of easily manufacturing a nano alloy catalyst having a new composition beyond a conventional catalyst characteristic and of applying the nano alloy catalyst to a metal oxide nano structure to easily change sensitization degree of relative sensitivity according to whether the catalyst is included or not.

SUMMARY

Embodiments of the inventive concepts may provide a method of providing hetero-catalyst metal particles into an apo-ferritin corresponding to ferritin protein not combined with iron and of fastening the apo-ferritin including the hetero-catalyst metal particles to the inside of a metal oxide semiconductor nanofiber. In particular, embodiments of the inventive concepts may provide a technique of synthesizing a super-sensitivity nanofiber sensing materials including the hetero-catalyst metal particles which are uniformly distributed in the inside and on a surface of the metal oxide semiconductor nanofiber without aggregation thereof after a high-temperature thermal treatment and of which each shows a chemical sensitization effect and an electronic sensitization effect at the same time to have a better catalyst effect than a mono-catalyst, and a gas sensor application technique using the same.

These techniques may be provided to solve conventional problems and may prevent aggregation between catalyst particles having sizes of 8 nm or less to maximize activation of the catalyst. Thus, embodiments of the inventive concepts may also provide a member for a gas sensor which can be manufactured in bulk through simple manufacturing processes and a high-sensitivity characteristic detecting a very small amount of gas, a gas sensor using the same, and a manufacturing method thereof.

In one aspect of the inventive concepts, hetero nanoparticle catalysts having both chemical and electronic sensitization effects of a catalyst or excellent catalyst characteristics unexpected in a mono catalyst, and the manufactured hetero nanoparticle catalysts are uniformly fastened to an inside and a surface of one-dimensional metal oxide semiconductor nanofibers to provide a sensing material in which the hetero nanoparticle catalysts are uniformly distributed without aggregation, and a member for a gas sensor using the same. A method of manufacturing the sensing materials or the member for a gas sensor according to the inventive concepts may include: (a) synthesizing hetero nanoparticle catalysts using apo-ferritins; (b) manufacturing an electrospinning solution in which the apo-ferritins including the hetero nanoparticle catalysts, a metal oxide precursor and a polymer are dissolved; (c) manufacturing a metal oxide precursor/polymer/hetero nanoparticle catalyst complex fiber, in which the hetero nanoparticle catalysts are contained in a surface and/or the inside of a metal oxide precursor/polymer complex nanofibers, by means of an electrospinning method; (d) performing a thermal treatment process to remove the polymer and protein constituting the apo-ferritins and to oxidize the metal oxide precursor, thereby forming one-dimensional metal oxide semiconductor nanofibers to which the hetero nanoparticle catalysts are fastened; (e) pulverizing the metal oxide semiconductor nanofibers having the fastened hetero nanoparticle catalysts to coat an electrode for gas sensor measurement with the pulverized metal oxide semiconductor nanofibers; (f) manufacturing a plurality of gas sensor arrays using a plurality of the metal oxide semiconductor nanofibers to which the hetero nanoparticle catalysts are fastened.

Here, in step (a), the apo-ferritin may have a sphere protein shape of which the inside is empty, and various metal ions may be provided in the inside of the apo-ferritin by a substitution method. The substituted metal ions may be reduced to form a metal particle catalyst. In particular, the apo-ferritin may be colorless protein existing in mucosa cells of the small intestine and may have a diameter of 12 nm. The apo-ferritin may have a hollow shape with an inner cavity diameter of 8 nm. One, two or more kinds of metal ions may be provided in the apo-ferritin by a substitution process, so a mono or hetero metal catalyst may be included in the apo-ferritin. Sizes of nano catalysts may be adjusted in a range of 0.1 nm to 8 nm by adjusting a concentration of an apo-ferritin water solution and a concentration of the nano catalysts synthesized within the apo-ferritins, and the apo-ferritins containing hetero nanoparticle catalysts may be dispersed in a solvent to have a concentration of 0.000001% to 50% with respect to the solvent or a concentration of 0.00001% to 50% with respect to a metal oxide.

In addition, in step (a), a kind or a shape of a metal salt to be provided into the apo-ferritin may be various. A representative salt-shaped catalyst may include platinum (IV) chloride, platinum(II) acetate, gold(I, III) chloride, gold(III) acetate, silver chloride, silver acetate, Iron(III) chloride, Iron(III) acetate, yttrium(III) nitrate hexahydrate, nickel(II) chloride, nickel(II) acetate, ruthenium(III) chloride, ruthenium acetate, iridium(III) chloride, iridium acetate, tantalum(V) chloride, or palladium(II) chloride. However, if the salt includes a specific metal ion, the kind of the salt is not limited to a specific kind. When a mono metal salt is used, a mono metal particle may be formed in the hollow region of the apo-ferritin. In an embodiment, a nanoparticle may be synthesized within the apo-ferritin by using two metal salts. In this case, if the apo-ferritin includes metals of which each has strong bonding strength between the same kinds of metal atoms, phase segregation may occur to form a hetero metal catalyst having segregated phases in the apo-ferritin. Alternatively, if metals easily bonded to a different kind of a metal are used in the apo-ferritin, the hetero nanoparticle catalyst of a metal alloy form may be synthesized in the hollow region of the apo-ferritin. In particular, in the hetero nanoparticle catalyst having the phases segregated from each other by the strong bonding strength between the same kinds of metal atoms, a metal-metal nanoparticle catalyst may be formed when metals not oxidized during a thermal treatment process for synthesizing the sensing material using nanoparticles are used, or a metal-metal oxide nanoparticle catalyst may be formed when a metal not oxidized and a metal oxidized during the thermal treatment process are used. Alternatively, if all of the two metals are oxidized after the thermal treatment process, a metal oxide-metal oxide nanoparticle catalyst may be formed.

When the hetero nanoparticle catalyst has a single crystal structure by great bonding strength between different kinds of metals and different kinds of atoms of the hetero nanoparticle catalyst are easily substituted for each other, the hetero nanoparticle catalyst may have an intermetallic compound particle shape of which components have a simple constant ratio or may have a solid solution or nanoalloy shape of which component have a non-constant ratio.

Since the apo-ferritin including the hetero nanoparticle catalyst synthesized by performing a reduction process to different kinds of the metal salts included in the hollow region has a shell made of protein, the apo-ferritins may be easily dispersed in the water solution.

Furthermore, in step (a), the protein of the shell of the apo-ferritin may be completely removed during a high-temperature thermal treatment process. In particular, when the metal oxide semiconductor nanofiber is synthesized using an electrospinning method, the high-temperature thermal treatment process should be performed. At this time, the shells, made of protein, of the apo-ferritins may be completely removed. In addition, fine pores corresponding to thicknesses of the shells of the apo-ferritins may be formed when the protein shells of the apo-ferritins are removed. Thus, a plurality of the fine pores may be contained in the metal oxide semiconductor nanofibers including the hetero nanoparticle catalysts.

In step (b) for manufacturing the spinning solution for the electrospinning process, the complex spinning solution in which the metal oxide precursor (metal salt) and the polymer are dissolved may be manufactured. At this time, kinds of the metal oxide precursor and the polymer may be changed to form another complex spinning solution. In particular, the apo-ferritins including hetero metal particles synthesized in step (a) may be added to manufacture the electrospinning solution. A concentration of the apo-ferritins including the hetero nanoparticle catalysts added to the metal oxide precursor/polymer complex electrospinning solution may range from 0.001 wt % to 50 wt %.

In step (c), polymer nanofibers containing at least one of various kinds of metal oxide precursors may be formed using the electrospinning method, and the apo-ferritins may be uniformly distributed within the inside and on an outer wall of the polymer nanofibers due to an excellent dispersion characteristic of the apo-ferritins. The apo-ferritins including the hetero nanoparticle catalysts may be mainly distributed in the inside of the metal oxide precursor/polymer complex nanofibers, some of the apo-ferritins may be exposed on the outer wall of the complex nanofibers.

In addition, in step (c), during the electrospinning process, the complex nanofibers may be discharged through a plurality of nozzles of a nozzle electrospinning unit or may be discharged using a wire-type or a cylinder-type electrospinning unit. As a result, the metal oxide precursor/polymer complex nanofibers including the apo-ferritins including the hetero nanoparticle catalysts may be manufactured.

In step (d), the high-temperature thermal treatment process may be performed on the metal oxide precursor/polymer complex nanofibers having a one-dimensional structure, so the polymer may be decomposed and removed and the metal oxide precursor may be oxidized to form the metal oxide nanofibers having a one-dimensional structure.

In addition, in step (d), the high-temperature thermal treatment process may be performed on the metal oxide precursor/polymer complex nanofibers including the apo-ferritins including the hetero nanoparticle catalysts at a temperature of 400 degrees Celsius to 800 degrees Celsius. During the high-temperature thermal treatment process, the polymer constituting the complex nanofibers may be decomposed and removed, the metal oxide precursor may be oxidized to form the metal oxide semiconductor nanofibers, and the protein shells of the apo-ferritins may be completely removed. In step (d), by the above processes, it is possible to obtain the metal oxide semiconductor nanofibers having the inside and the partial outer wall to which the hetero nanoparticle catalysts included in the apo-ferritins are uniformly fastened without aggregation.

Furthermore, in step (d), the hetero nanoparticle catalysts uniformly fastened to the inside of the metal oxide nanofibers may have at least one of a metal-metal catalyst nanoparticle, a metal-metal oxide catalyst nanoparticle, or a metal oxide-metal oxide catalyst nanoparticle. The hetero nanoparticle catalyst formed in the hollow region of the initial apo-ferritin may have a segregation shape where phases are segregated from each other by the strong bonding strength between the same kinds of metal atoms, or a metal alloy shape where different kinds of metal atoms are easily combined with each other by the strong bonding strength between the different kinds of metal atoms.

In the hetero nanoparticle catalyst of which the phases are segregated from each other by the strong bonding strength between the same kinds of metal atoms, most of metals except some noble metals may be oxidized to be converted into metal oxides after the thermal treatment process is performed in air. If one selected from a group consisting of Rh, Ni, Co, Cu, Fe, Ti, Zn, Sn, V, Cr, Mo or W is one component of an alloy, a metal oxide (e.g., $Rh_2O_3$, NiO, $Co_3O_4$, CuO, $Fe_2O_3$, $Fe_3O_4$, $TiO_2$, ZnO, $SnO_2$, $V_2O_5$, $V_2O_3$, $Cr_2O_3$, $MoO_3$ or $WO_3$) may be formed after the high-temperature thermal treatment process. Since the metal oxide has a semiconductor characteristic such as an N-type characteristic or a P-type characteristic, it may allow the sensing material to have a catalyst characteristic.

In detail, when each of the components of the hetero nanoparticle catalyst included in the apo-ferritin is selected from a M' group (Pt and Au) and a M" group (Ag, Pd, Ru, Ir, Y, In, Rh, Ni, Co, Cu, Fe, Ti, Zn, Sn, V, Cr, Mo, and W), the M' (Pt and Au) group may be maintained in a metal form after the thermal treatment process. In this case, the hetero nanoparticle catalyst may be expressed by $1M'_x$-$2M'_{1-x}$, where "X" is in a range of 0.01 atomic percent (at %) to 99.99 at %. Here, each of "1M'" and "2M'" means one metal catalyst selected from the group consisting of Pt and Au. As described above, the M" group (Ag, Pd, Ru, Ir, Y, In, Rh, Ni, Co, Cu, Fe, Ti, Zn, Sn, V, Cr, Mo, and W) may be the metals which are changed into the conductive metal oxide or the metal oxide having the semiconductor characteristic after the thermal treatment process. Thus, when each of the components of the hetero nanoparticle catalyst included in the apo-ferritin is selected from the M" group (Ag, Pd, Ru, Ir, Y, In, Rh, Ni, Co, Cu, Fe, Ti, Zn, Sn, V, Cr, Mo, and W), the hetero nanoparticle catalyst after the thermal treatment process may include a M"O component corresponding to an oxide of the M" metal. Here, "M"O" is defined as an oxide formed by the oxidation during the thermal treatment process. The M"O is a metal oxide expressed by a chemical formula $M''_YO_Z$ where "Y" is an integer equal to or greater than 1 and equal to or less than 3, and "Z" is an integer equal to or greater than 1 and equal to or less than 5. In an embodiment, the hetero nanoparticle catalyst after the thermal treatment process may include at least two selected from a group consisting of N-type metal oxides (e.g., $TiO_2$, ZnO, $WO_3$, $SnO_2$, $IrO_2$, $In_2O_3$, $V_2O_3$, and $MoO_3$) and P-type metal oxides (e.g., $Ag_2O$, PdO, $RuO_2$, $Rh_2O_3$, NiO, $Co_3O_4$, CuO, $Fe_2O_3$, $Fe_3O_4$, $V_2O_5$, and $Cr_2O_3$). When two metals oxidized after the thermal treatment process are used, the hetero nanoparticle catalyst may be formed of a metal oxide expressed by a chemical formula $1M''_YO_Z$-$2M''_YO_Z$. At this time, "Y" is an integer equal to or greater than 1 and equal to or less than 3 and "Z" is an integer equal to or greater than 1 and equal to or less than 5. In an embodiment, "$1M''_YO_Z$" and "$2M''_YO_Z$" may be one of the N-type metal oxides and one of the P-type metal oxides, respectively. In another embodiment, all of "$1M''_YO_Z$" and "$2M''_YO_Z$" may be the N-type metal oxides. In still another embodiment, all of "$1M''_YO_Z$" and "$2M''_YO_Z$" may be the P-type metal oxides. In other words, "$1M''_YO_Z$" and "$2M''_YO_Z$" may have any combination of the N-type metal oxides and the P-type metal oxides.

When the hetero nanoparticle included in the hollow region of the apo-ferritin consists of one metal selected from the M' group and one metal selected from the M'' group, the one metal selected from the M'' group may be changed into the M''O form during the thermal treatment process, thereby forming the metal-metal oxide complex nanoparticle catalyst expressed by a chemical formula $1M''_x$-$2M''_YO_Z$, where "X" is in a range of 0.01 at % to 99.99 at %, "Y" is an integer equal to or greater than 1 and equal to or less than 3, and "Z" is an integer equal to or greater than 1 and equal to or less than 5. Here, 1M'' is one selected from the metals listed above, and 2M''O is one selected from the metal oxides listed above. At this time, the metal oxide expressed by $2M''_YO_Z$ may include one selected from a group consisting of the N-type metal oxides and the P-type metal oxides.

If the hetero nanoparticle catalyst is formed in the metal alloy form having the strong bonding strength between the different kinds of the metal atoms, the metal component M and the metal component M' constituting the hetero nanoparticle catalyst may be formed into an intermetallic compound having a simple constant ratio of $M_xM'_Y$. Here, the metal component M and the metal component M' mean metals different from each other, and each of "X" and "Y" may be an integer ranging from 1 to 99. Alternatively, the hetero nanoparticle catalyst may be formed in a nanoalloy form expressed by $M_xM'_{1-x}$ having a non-constant ratio. Here, "X" may be in a range of 0.01 to 0.99.

In another aspect, a method of manufacturing a gas sensor using a metal oxide semiconductor nanoliber sensing materials which include hetero nanoparticle catalysts and has a one-dimensional structure may include (e) pulverizing the metal oxide semiconductor nanofibers having the fastened hetero nanoparticle catalysts to coat an electrode for gas sensor measurement with the pulverized metal oxide semiconductor nanofibers; (f) manufacturing a plurality of gas sensor arrays using a plurality of the metal oxide semiconductor nanofibers to which the hetero nanoparticle catalysts are fastened.

Here, in step (e) of coating the one-dimensional structural porous nanofibers on the sensor substrate, the metal oxide semiconductor nanofibers including the hetero nanoparticle catalysts may be pulverized by a ball-milling process or an ultrasonic pulverization process, so a long fiber may be converted into short fibers. The short fibers may be coated on the sensor substrate having sensing electrodes for analyzing an electrical resistance by a spray coating method, a drop coating method, a screen printing method, an electrohydrodynamic coating method, an inkjet printing method, a direct coating method using an electrospinning method, or a transfer coating method. However, the inventive concepts are not limited thereto. The coating method may be one of other coating methods capable of coating the sensing material based on the metal oxide nanofibers including the hetero nanoparticle catalysts on the sensor substrate.

In still another aspect, formation of the metal oxide nanofibers having the one-dimensional structure may be performed by a process of mixing various kinds of metal oxide precursors and various kinds of polymers and a high-temperature thermal treatment process. For example, the metal oxide nanofibers may include at least one of ZnO, $SnO_2$, $WO_3$, $Fe_2O_3$, $Fe_3O_4$, NiO, $TiO_2$, CuO, $In_2O_3$, $Zn_2SnO_4$, $CO_3O_4$, $LaCoO_3$, $NiCo_2O_4$, $Ca_2Mn_3O_8$, $ZrO_2$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Li_{0.3}La_{0.57}TiO_3$, $LiV_3O_8$, $InTaO_4$, $InTaO_4$, $Ga_2O_3$, $LiNiO_2$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}Co_{0.8}Fe_{0.2}O_{3-7}$.

In an embodiment, the metal oxide nanofibers having the one-dimensional structure may have a diameter ranging from 50 nm to 10 μm and a length ranging from 1 μm to 500 μm.

In an embodiment, the nanofibers may have a dense poly-crystalline nanofiber shape or may have high-porous poly-crystalline nanofibers having a lot of pores. Alternatively, the nanofibers may have a short-fiber shape by the pulverization process.

In an embodiment, one or more nanofiber(s) may constitute a nanofiber-network shape. At this time, the pore may be formed between the nanofibers.

In yet another aspect, a metal oxide nanofiber sensing material including the hetero nanoparticle catalysts synthesized using the apo-ferritins may form a member for a gas sensor according to the inventive concepts and may measure a concentration of a specific gas.

Here, the manufactured sensing material includes the hetero nanoparticle catalysts very uniformly distributed on the surface and/or in the inside of the one-dimensional metal oxide nanofibers. Thus, sensitivity of the sensing material may be maximized by the uniform dispersion of the hetero nanoparticle catalysts without aggregation and characteristics of the hetero nanoparticle catalysts. As a result, the sensing material may have an excellent gas sensing characteristic.

Here, the gas sensor based on the metal oxide nanofibers including the hetero nanoparticle catalysts may sense a specific volatile organic compound gas released from exhaled breath of the men to diagnose a disease occurs in the men or not and may sense a harmful environment gas indoor and outdoor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The inventive concepts will become more apparent in view of the attached drawings and accompanying detailed description.

DETAILED DESCRIPTION OF THE EMBODIMENTS

Figure 1:
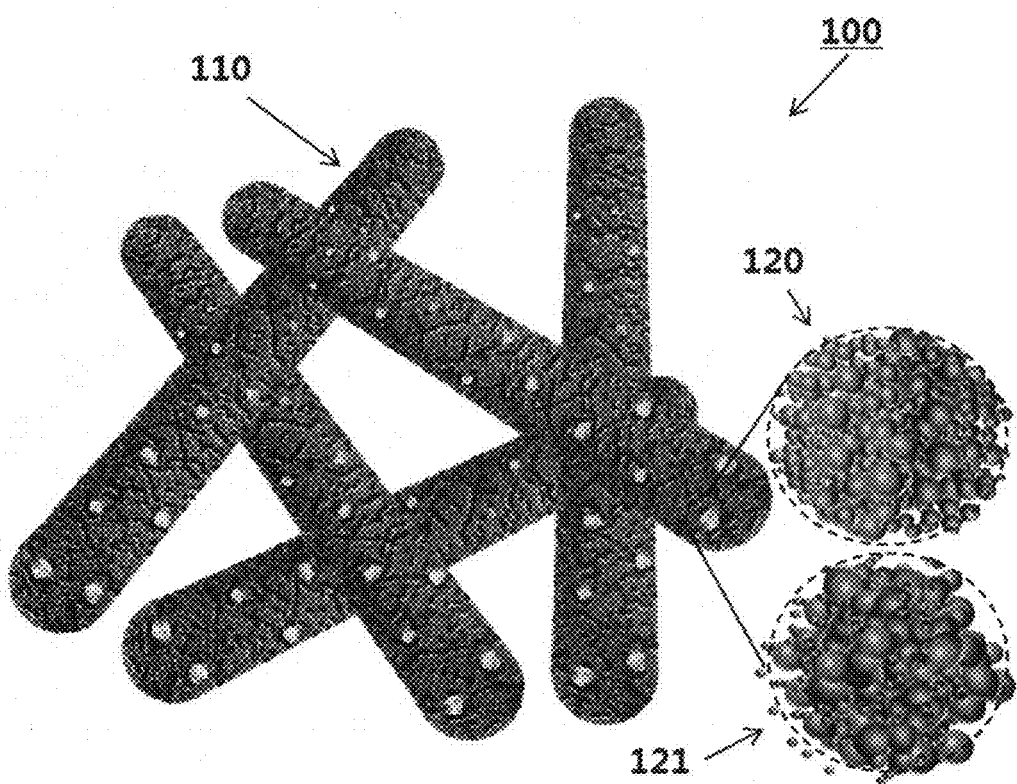
FIG. 1 is a schematic diagram showing metal oxide semiconductor nanofibers including a hetero nanoparticle catalyst synthesized using an apo-ferritin in accordance with an embodiment of the inventive concepts.

The inventive concepts will now be described more fully hereinafter with reference to the accompanying drawings, in which exemplary embodiments of the inventive concepts are shown. The advantages and features of the inventive concepts and methods of achieving them will be apparent from the following exemplary embodiments that will be described in more detail with reference to the accompanying drawings. It should be noted, however, that the inventive concepts are not limited to the following exemplary embodiments, and may be implemented in various forms. Accordingly, the exemplary embodiments are provided only to disclose the inventive concepts and let those skilled in the art know the category of the inventive concepts. In the drawings, embodiments of the inventive concepts are not limited to the specific examples provided herein and are exaggerated for clarity.

The terminology used herein is for the purpose of describing particular embodiments only and is not intended to limit the invention. As used herein, the term "and/or" includes any and all combinations of one or more of the associated listed items. As used herein, the singular terms "a," "an" and "the" are intended to include the plural forms as well, unless the context clearly indicates otherwise. General descriptions to known techniques may be omitted to clarify the features of the inventive concepts.

It will be also understood that although the terms first, second, third etc. may be used herein to describe various elements, these elements should not be limited by these terms. These terms are only used to distinguish one element from another element.

Hereinafter, a metal oxide semiconductor nanostructure including a hetero nanoparticle catalyst synthesized using an apo-ferritin, a member for a gas sensor using the same, a gas sensor using the same, and a manufacturing method thereof will be described in more detail with reference to the accompanying drawings.

According to embodiments of the inventive concepts, a hetero nanoparticle catalyst having a size ranging from 0.1 nm to 8 nm may be synthesized using apo-ferritin protein, and the hetero nanoparticle catalyst and an electrospinning solution may be injected to fasten the hetero nanoparticle catalyst to the inside and a partial surface of a one-dimensional porous metal oxide semiconductor nanofibers. The nanofibers having the hetero nanoparticle catalyst may be used as a sensing material for a gas sensor. In a conventional art, researches increasing a surface area of a one-dimensional structure and using a catalyst have been conducted to improve a gas sensing characteristic and selectivity of a metal oxide semiconductor. For example, researches using the catalyst have been conducted for a chemical sensitization method increasing a concentration of adsorption ions using a metal catalyst (e.g., platinum or gold) or an electronic sensitization method improving sensitivity based on an oxidation number variation of palladium or silver. However, by a conventional method of fastening the metal or metal oxide catalyst, the nano catalyst may not be manufactured to have a size of several nanometers and may not be uniformly distributed on an entire area of a sensing material. In addition, it is impossible to obtain the chemical sensitization effect and the electronic sensitization effect at the same time through the conventional fastening method.

To overcome these disadvantages, according to embodiments of the inventive concepts, the hetero nanoparticle catalyst may be synthesized using the apo-ferritin, the synthesized hetero nanoparticle catalyst may mixed with an electrospinning solution including a metal precursor and a polymer, and the mixture may go through an electrospinning process and thermal treatment process to manufacture a porous metal oxide semiconductor in which the hetero nanoparticle is uniformly included. The apo-ferritin may be formed of protein and may have a spherical shape of which the inside is empty or hollow. Various ions may be provided into the empty space of the apo-ferritin. In addition, hetero metallic salt ions may be provided into the empty space of the apo-ferritin by a replacement method, the replaced hetero metallic salt ions may be treated by a reduction treatment process to form a structure or metal alloy in which metals of the hetero nanoparticle catalyst are combined with each other.

A size of the hetero nanoparticle catalyst synthesized using the apo-ferritin may range from 0.1 nm to 8 nm, and the hetero nanoparticle catalyst included in the inside of the apo-ferritin may have a form in which two different kinds of metals are combined with each other in a state where they are segregated from each other, or an alloy form in which two different kinds of metal atoms are replaced with each other so as to be strongly combined with each other. In the case that the two different kinds of the metals constitute the nanoparticle of the hetero nanoparticle catalyst in the state where they are segregated from each other by the interface, a portion of the metals may be oxidized to form a metal oxide catalyst. Thus, a metal-metal complex catalyst, a metal-metal oxide complex catalyst, or a metal oxide-metal oxide complex catalyst may be realized, so the electronic sensitization and the chemical sensitization of the catalyst may be obtained together.

In addition, in the case that the hetero nanoparticle catalyst has the alloy form in which the two different kinds of the metals are strongly combined with each other by the replacement, it may have a nanoparticle shape formed of an intermetallic compound or a solid solution. In this case, the hetero nanoparticle catalyst may show properties of a completely new synthesis material, not properties of a mono catalyst, and sensitivity of the hetero nanoparticle catalyst as the new catalyst may be better than that of a conventional catalyst.

Since nanoparticles of the synthesized hetero nanoparticle catalyst are encapsulated by the protein constituting the apo-ferritin, they are not aggregated when dispersed in the electrospinning solution but are uniformly distributed, thereby maximizing the effect of the catalyst in the sensing material. Since the hetero nanoparticle catalyst manufactured using the apo-ferritin is uniformly fastened on the metal oxide semiconductor nanofibers, it is possible to realize a member for a gas sensor which has a high-sensitivity characteristic capable of detecting a very small amount of a gas and excellent selectivity capable of selectively detecting various gases and is mass-produced by an effective process, a gas sensor using the same, and a manufacturing method thereof.

FIG. 1 is a schematic diagram showing a member for a gas sensor which uses a metal oxide semiconductor nanofibers including a hetero nanoparticle catalyst according to an embodiment of the inventive concepts. FIG. 1 shows a member 100 for a gas sensor which is formed using a metal oxide semiconductor nanofiber 110 having a one-dimensional shape. However, the inventive concepts are not limited thereto. In other embodiments, a member for a gas sensor which have another shape may be formed using a nanostructure having a nanotube or nanorod synthesized using an electrospinning technique.

Since hetero nanoparticle catalyst 120 synthesized using the apo-ferritin is uniformly dispersed in an electrospinning solution, the hetero nanoparticle catalyst 120 and the electrospinning solution mixed with a metal oxide precursor and a polymer may be electrospun to manufacture metal oxide precursor-polymer complex nanofibers in which the hetero nanoparticle catalyst 120 is embedded. A thermal treatment process may be performed on the manufactured metal oxide precursor-polymer complex nanofibers at high temperature to obtain the metal oxide semiconductor nanofibers 110 including the hetero nanoparticle catalyst 120 uniformly distributed in the inside and on the surface of the metal oxide semiconductor nanofibers 110.

A ferritin is sphere-shaped protein enzyme consisting of 24 polypeptides. The protein enzyme is enzyme adjusting an iron (Fe) content in the body and contains about 4500 iron minerals in protein. The ferritin from which the iron is electrically or chemically removed may be called 'the apo-ferritin'. A metal (e.g., Au, Pt, Pd, Ru, Y, Cu, Ag, Co, and/or Ni may be provided into the inside of the apo-ferritin by a chemical method. The nano metal manufactured using the apo-ferritin as described above may have a very small size ranging from 0.1 nm to 8 nm. In addition, since the hetero nanoparticle catalyst 120 is encapsulated by the apo-ferritin protein before the thermal treatment process described above, the apo-ferritins including the nano catalyst particles may be uniformly dispersed in the electrospinning solution without aggregation therebetween. The nano catalyst particle to be applied to the sensing material may be a noble metal (e.g., Pt or Au)-based catalyst particle that accelerates a decomposition reaction of an oxygen molecule to increase a concentration of adsorption ions participating a surface reaction or may be a catalyst particle that has a catalyst reaction by an oxidation process of Ag—$Ag_2O$ or Pd—PdO affecting improvement of the sensitivity characteristic. In addition, when the hetero nanoparticle catalyst 120 containing the noble metal catalyst and the oxide catalyst segregated from each other is synthesized using the apo-ferritin and is then added into the metal oxide nanofibers, the chemical sensitization effect and the electrical sensitization effect may be obtained at the same time. Furthermore, during the thermal treatment process, a metal (e.g., Ru, Ir, Ag, In, Rh, Ni, Co, Cu, Fe, Ti, Zn, Sn, V, Cr, Mo, and/or W) may be converted into a metal oxide to obtain characteristics of a metal oxide catalyst including $RuO_2$, $IrO_2$, $Ag_2O$, $In_2O_3$, $Rh_2O_3$, NiO, $Co_3O_4$, CuO, $Fe_2O_3$, $Fe_3O_4$, $TiO_2$, ZnO, $SnO_2$, $V_2O_5$, $V_2O_3$, $Cr_2O_3$, $MoO_3$, and/or $WO_3$.

In addition, the hetero nano alloy catalyst particle (e.g., PtAu, PtPd, RhPd, PdRu, PtCu, PtY, PtAg, PtCo, or PtFe) of which metals are strongly combined with each other and are not segregated from each other to constitute the alloy form may correspond to a new catalyst having a new composition which is not reported and may have a higher sensitivity than a conventional mono catalyst so as to be used in a high-performance sensor.

When the apo-ferritins including the fine hetero nanoparticle catalysts 120 are fastened to the metal oxide semiconductor nanofibers 110, it is possible to obtain an effect of doping the inside of the apo-ferritin with the hetero nanoparticle catalyst 120. In addition, the apo-ferritins may be easily dispersed unlike catalyst particles synthesized using a general polyol process, so the nano catalyst particles may be easily added into the metal oxide semiconductor nanofibers 110 without aggregation. Furthermore, the metal oxide semiconductor nanofibers 110 may go through a Sol-Gel reaction during the thermal treatment process to have a poly-crystalline metal oxide nanofiber shape through nucleation and grain growth.

The metal ions included in the empty central space of the apo-ferritin may include at least one or two of Pt, Au, Ag, Fe, Ni, Ti, Y, Sn, Si, Al, Cu, Mg, Sc, V, Cr, Mn, Co, Zn, Sr, W, Ru, Rh, Ir, Ta, Sb, In, Pb, or Pd. The metal ions included in the apo-ferritins may be formed into the hetero nanoparticle catalyst 120 of the segregation form and the hetero nanoparticle catalyst 121 of the alloy form. These nanoparticle catalysts may be finally formed into one nanoparticle catalyst 120 selected from a group consisting of a metal-metal complex catalyst in the segregation form, a metal-metal oxide complex catalyst in the segregation form, and a metal oxide-metal oxide complex catalyst in the segregation form. For example, the metal-metal oxide nanoparticle catalyst may include $Pt/IrO_2$, $Pt/RuO_2$, $Pt/Rh_2O_3$, Pt/NiO, $Pt/CO_3O_4$, Pt/CuO, $Pt/Ag_2O$, $Pt/Fe_2O_3$, $Au/IrO_2$, $Au/RuO_2$, $Au/Rh_2O_3$, Au/NiO, $Au/Co_3O_4$, Au/CuO, or $Au/Ag_2O$. For example, the metal-metal nanoparticle catalyst may include Pt/Au. For example, the metal oxide-metal oxide nanoparticle catalyst may be a metal oxide catalyst that consists of two selected from a group consisting of N-type metal oxides (e.g., $TiO_2$, ZnO, $WO_3$, $SnO_2$, $IrO_2$, $In_2O_3$, $V_2O_3$, and $MoO_3$) and P-type metal oxides (e.g., $Ag_2O$, PdO, $RuO_2$, $Rh_2O_3$, NiO, $Co_3O_4$, CuO, $Fe_2O_3$, $Fe_3O_4$, $V_2O_5$, and $Cr_2O_3$). At this time, the nanoparticle catalyst 120 may have a size ranging from 0.1 nm to 8 nm. In hetero nanoparticle catalyst combinations of the metal-metal ($1M'_x$-$2M'_{1-x}$), the metal-metal oxide ($1M'_x$-$2M''_yO_z$), and the metal oxide-metal oxide ($1M''_yO_z$-$2M''_yO_z$). "X" is in a range of 0.01 to 99.99, "Y" is an integer equal to or greater than 1 and equal to or less than 3, and "Z" is an integer equal to or greater than 1 and equal to or less than 5. Here, the combination of the metal oxide-metal oxide may include a combination of an N-type metal oxide and an N-type metal oxide, a combination of an N-type metal oxide and a P-type metal oxide, and/or a combination of a P-type metal oxide and a P-type metal oxide. The metal and the metal oxide are classified based on the final catalyst obtained after the thermal treatment process and may include any combination of the materials described above.

In the case that the different kinds of materials are easily combined with each other to form the hetero nanoparticle catalyst 121 of the metal alloy form having strong bonding strength, metal components M and M' constituting the catalyst 121 may have a form of an intermetallic compound having a simple constant ratio of $M_xM'_y$. Here, "M" and "M'" denote metal components different from each other, and each of "X" and "Y" is an integer ranging from 1 to 99. Alternatively, in the hetero nanoparticle catalyst 121, the components may form a nanoalloy of $M_xM'_{1-x}$ which does not have a constant ratio. Here, "X" is in a range of 0.01 to 0.99.

The metal oxide semiconductor nanofibers corresponding to the nanostructure may include a material of which electrical conductivity or an electrical resistance characteristic is changeable by adsorption and desorption of a gas. In particular, the metal oxide semiconductor nanofibers may include at least one of ZnO, $SnO_2$, $WO_3$, $Fe_2O_3$, $Fe_3O_4$, NiO, $TiO_2$, CuO, $In_2O_3$, $Zn_2SnO_4$, $Co_3O_4$, PdO, $LaCoO_3$, $NiCo_2O_4$, $Ca_2Mn_3O_8$, $V_2O_5$, $Cr_2O_3$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}Co_{0.8}Fe_{0.2}O_{3-7}$.

A super-sensitivity sensor monitoring harmful environment and diagnosing exhaled breath may be realized using the member 100 for a gas sensor which uses the metal oxide semiconductor nanofibers 110 including the hetero nanoparticle catalysts 120 and 121. When the member 100 for a gas sensor is manufactured, the apo-ferritins including the hetero nanoparticle catalysts 120 and 121 may be included into the metal oxide semiconductor nanofibers 110 and shells of the apo-ferritins may be pyrolyzed and removed by the thermal treatment process to uniformly fasten the hetero nanoparticle catalysts 120 and 121 to the surface and the inside of the metal oxide semiconductor nanofibers. The member 100 for a gas sensor using the metal oxide semiconductor nanofibers 110 including the hetero nanoparticle catalysts 120 and 121 may be formed by the processes described above, and the super-sensitivity sensor monitoring the harmful environment and diagnosing the exhaled breath may be realized using the member 100 for a gas sensor. At this time, the super-sensitivity sensor monitoring the harmful environment gas and diagnosing the exhaled breath may include a gas sensing material formed using the metal oxide semiconductor nanofibers 110 including the hetero nanoparticle catalysts 120 and 121, and a resistance measuring unit connected to the gas sensing material.

Figure 2:
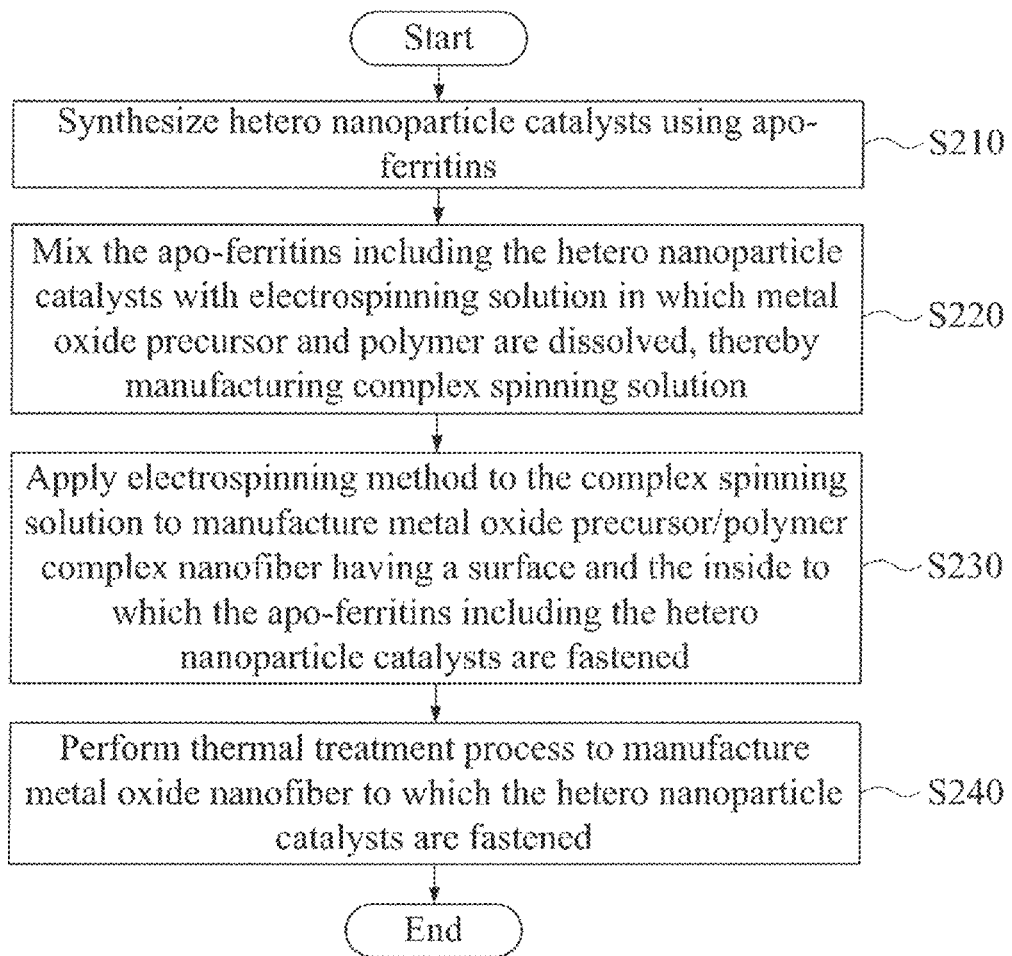
FIG. 2 is a flow chart showing a method of manufacturing a member for a gas sensor using metal oxide semiconductor nanofibers including a hetero nanoparticle catalyst synthesized using an apo-ferritin in accordance with an embodiment of the inventive concepts.

FIG. 2 is a flow chart showing a method of manufacturing a member for a gas sensor using metal oxide semiconductor nanofibers including a hetero nanoparticle catalyst through an electrospinning method in accordance with an embodiment of the inventive concepts. As shown in the flow chart of FIG. 2, the method of manufacturing the member for a gas sensor may include synthesizing hetero nanoparticle catalysts using apo-ferritins (S210), mixing the apo-ferritins including the synthesized hetero nanoparticle catalysts with an electrospinning solution including a metal precursor and a polymer to manufacture a complex spinning solution (S220), applying an electrospinning method to the complex spinning solution to manufacture a metal precursor/polymer complex nanofibers having a surface and the inside to which the apo-ferritins including the hetero nanoparticle catalysts are fastened (S230), and performing a thermal treatment process to manufacture a metal oxide nanofiber complex to which the hetero nanoparticle catalysts are fastened (S240). Hereinafter, the steps will be described in more detail.

First, synthesizing the hetero nanoparticle catalysts using the apo-ferritins (S210) will be described in detail.

The apo-ferritin used in the step S210 may include a ferritin extracted from the equine spleen and/or may be formed using a ferritin obtained regardless of the human liver or the human spleen. Iron ions in the obtained ferritin may be removed to form the apo-ferritin. The iron ions in the ferritin may be removed by a chemical method and/or an electrical method. A solution for keeping the apo-ferritins including empty insides (i.e., a hollow structures) may include a saline solution, e.g., at least one of NaCl solutions having various concentrations. The apo-ferritins may be included in a solution having a basic pH in order to provide a metal salt into the apo-ferritin. In particular, the pH of the solution may range from 8.0 to 9.5, so the metal salt may be induced to be provided into the apo-ferritin by the chemical method. A concentration of the keeping solution (e.g., the saline solution) containing the apo-ferritin may range from 0.1 mg/ml to 200 mg/ml. A solvent used in the manufacture of the metal salt solution may be a compatible solvent such as ethanol, water, chloroform, N,N'-dimethylformamide, dimethylsulfoxide, N,N'-dimethylacetamide, or N-methylpyrrolidone. However, when the solvent is capable of dissolving the metal salt, the solvent is not limited to a specific solvent. A concentration of the metal salt solution may range from 0.1 mg/ml to 1000 mg/ml.

A kind and combination of the metal salt included in the apo-ferritin may be various. In some embodiments, a single kind of metal salt or two different kinds of metal salts may be provided into the apo-ferritin by a substitution method. The metal salt may include at least one of Pt, Au, Ag, Fe, Ni, Ti, Y, Sn, Si, Al, Cu, Mg, Sc, V, Cr, Mn, Co, Zn, Sr, W, Ru, Rh, Ir, Ta, Sb, In, Pb, or Pd and may be converted into a metal or a metal oxide after the thermal treatment process. In particular, a hetero nanoparticle catalyst of which two components are combined with each other but are segregated from each other (e.g., the hetero nanoparticle catalyst 120 of FIG. 1) may include a metal-metal shape, a metal-metal oxide shape, or a metal oxide-metal oxide shape after the thermal treatment process and may be fastened to the inside and a partial surface of the metal oxide nanofibers after the thermal treatment process. The hetero nanoparticle catalyst 120 may have a size ranging from 0.1 nm to 8 nm. The hetero nanoparticle catalyst 120 may be expressed by the metal-metal ($1M'_x$-$2M'_{1-x}$), the metal-metal oxide ($1M'_x$-$2M''_yO_Z$) and/or the metal oxide-metal oxide ($1M''_yO_Z$-$2M''_yO_Z$), where "X" is a range of 0.01 to 99.99, "Y" is an integer equal to or greater than 1 and equal to or less than 3, and "Z" is an integer equal to or greater than 1 and equal to or less than 5.

In the case that the different kinds of materials are easily combined with each other to form a hetero nanoparticle catalyst of the metal alloy form having strong bonding strength (e.g., the hetero nanoparticle catalyst of FIG. 1), metal components M and M' constituting the catalyst 121 may have a form of an intermetallic compound having a simple constant ratio of $M_XM'_Y$. Here, "M" and "M'" denote metal components different from each other, and each of "X" and "Y" is an integer ranging from 1 to 99. Alternatively, in the hetero nanoparticle catalyst 121, the components may form a nanoalloy of which does not have a constant ratio. Here, "X" is in a range of 0.01 to 0.99.

A reductant reducing the metal salt provided within the apo-ferritin may include a compatible reductant such as sodium borohydride ($NaBH_4$), lithium aluminum hydride ($LiAlH_4$), nascent (atomic) hydrogen, zinc-mercury amalgam (Zn(Hg)), oxalic acid ($C_2H_2O_4$), formic acid (HCOOH), ascorbic acid ($C_6H_8O_6$), sodium amalgam, diborane, or iron(II) sulfate.

Next, manufacturing the complex spinning solution in which the apo-ferritins including the synthesized hetero nanoparticle catalysts, the metal oxide precursor and the polymer are dissolved (S220) will be described in detail.

In the step S220, the apo-ferritins including the hetero nanoparticle catalysts, the metal precursor and the polymer may be dissolved to manufacture the complex spinning solution. Here, a solvent may include a compatible solvent (e.g., ethanol, water, chloroform, N,N'-dimethylformamide, dimethylsulfoxide, N,N'-dimethylacetamide, or N-methylpyrrolidone) and should dissolve the metal precursor and the polymer at the same time. If the polymer used in the step S220 is capable of being mixed with and dissolved in the metal precursor (e.g., a metal salt precursor) and the solvent, the polymer is not limited to a specific polymer.

The metal precursor used in the step S220 may include a precursor including a metal salt capable of forming a metal oxide nanofibers having a semiconductor property by the thermal treatment process. For example, the metal precursor may include at least one of, but not limited to, $ZnO$, $SnO_2$, $WO_3$, $Fe_2O_3$, $Fe_3O_4$, $NiO$, $TiO_2$, $CuO$, $In_2O_3$, $Zn_2SnO_4$, $Co_3O_4$, $PdO$, $LaCoO_3$, $NiCo_2O_4$, $Ca_2Mn_3O_8$, $V_2O_5$, $Cr_2O_3$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $InTaO_4$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, or $Ba_{0.5}Sr_{0.5}Co_{0.8}Fe_{0.2}O_{3-7}$.

For example, the polymer used in the step S220 may include at least one of polyurethane, polyurethane copolymer, cellulose acetate, cellulose, acetate butyrate, cellulose derivatives, polymethyl methacrylate (PMMA), polymethyl acrylate (PMA), polyacryl copolymer, poly(vinyl acetate) copolymer, polyvinyl acetate (PVAc), polyvinylpyrrolidone (PVP), polymethyl alcohol (PVA), poly furfuryl alcohol (PPFA), polystyrene (PS), polystyrene copolymer, polypropylene oxide (PEO), polypropylene oxide (PPO), polyethylene oxide copolymer, polypropylene oxide copolymer, polycarbonate (PC), polyvinylchloride (PVC), polycaprolactone, polyvinylidene fluoride, polyvinylidene fluoride copolymer, polyamide, or polyimide.

A weight ratio of the polymer:the hetero nanoparticle catalyst may range from 1:0.000001 to 1:0.5. A content of the apo-ferritins including the hetero nanoparticle catalysts may be determined depending on a kind of the hetero nanoparticle catalyst, a gas sensing characteristic according thereto, and selectivity according thereto. The member for a gas sensor which has improved characteristics may be manufactured using at least one of the various hetero nanoparticle catalysts.

When the complex spinning solution is manufactured under the conditions described above, the metal precursor and the apo-ferritins including the hetero nanoparticle catalysts may be firstly stirred into the solvent to uniformly mix the apo-ferritins including the hetero nanoparticle catalysts with a metal precursor solution, and then, the polymer may be stirred into the metal precursor solution including the apo-ferritins. The stirring process may be sufficiently performed at a temperature of a room temperature to 40 degrees Celsius for a time of 5 hours to 72 hours to uniformly mix the apo-ferritins including the hetero nanoparticle catalysts, the metal precursor and the polymer with each other. Thus, the complex spinning solution including the metal precursor, the polymer and the apo-ferritins including the hetero nanoparticle catalysts may be manufactured for the electrospinning process of the next step.

Next, the complex spinning solution may be electrospun to manufacture the metal precursor/polymer complex nanofibers to which the apo-ferritins including the hetero nanoparticle catalysts are uniformly fastened (S230). In an embodiment, the electrospinning method is used as the method of spinning the complex spinning solution. However, the inventive concepts are not limited thereto. In other embodiments, other method capable of manufacturing the nanofibers may be used in the step S230.

To electrospin the complex spinning solution including the apo-ferritins including the hetero nanoparticle catalysts, the metal precursor (e.g., the metal salt precursor) and the polymer, a syringe capable of quantitatively injecting the complex spinning solution may be filled with the complex spinning solution and then the complex spinning solution may be slowly discharged using a syringe pump at a constant rate. A syringe system may include the syringe, an injection needle connected to an end of the syringe, a high-voltage generator, and a grounded conductive substrate. The complex spinning solution may be electrospun by an electric field difference between the needle and a current collector. The solvent may be evaporated while the complex spinning solution is discharged by the electrospinning process, so a solid polymer fiber may be obtained and, at the same time, the metal precursor and the apo-ferritins including the hetero nanoparticle catalysts may be uniformly distributed in the inside and on an outer surface of the polymer fiber, thereby forming a complex nanofibers including the polymer fiber and the metal precursor and the apo-ferritins including the hetero nanoparticle catalysts. The complex nanofibers may have a web shape.

Next, in the step S240, the thermal treatment process may be performed on the metal precursor/polymer complex nanofibers to which the apo-ferritins including the hetero nanoparticle catalysts are uniformly fastened. In the step S240, the complex nanofibers may be thermally treated at a temperature ranging from 400 degrees Celsius to 800 degrees Celsius at which the polymer is pyrolyzed, and thus the polymer constituting the complex nanofibers and protein of shell portions of the apo-ferritins including the hetero nanoparticle catalysts may be pyrolyzed so as to be removed. At this time, the metal precursor may be oxidized to form metal oxide nanofibers, and the hetero nanoparticle catalyst included in the core of the apo-ferritin may be strongly fastened to the metal oxide semiconductor nanofibers 110 without aggregation.

Figure 3:
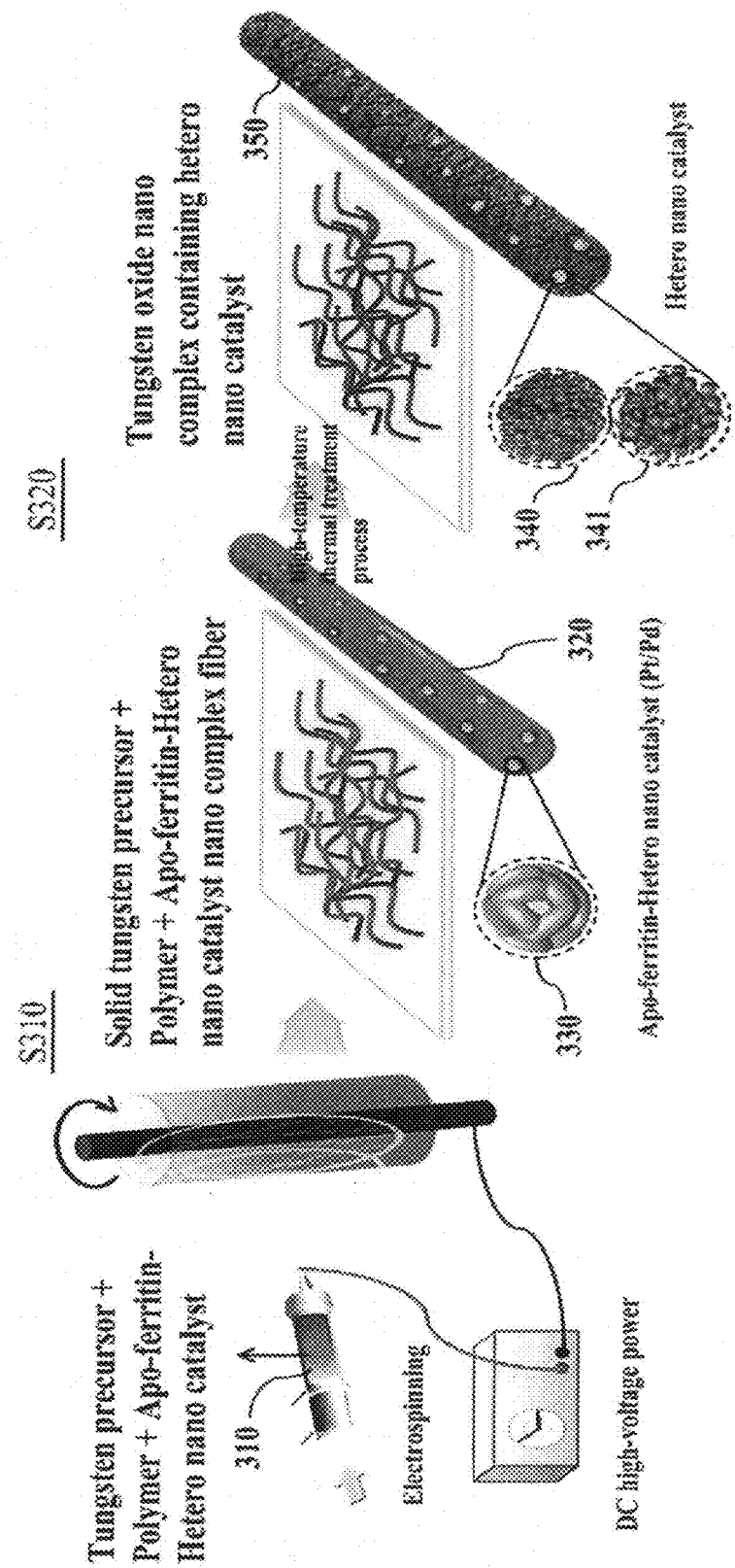
FIG. 3 is a diagram showing a method of manufacturing metal oxide semiconductor nanofibers including a hetero nanoparticle catalyst using an electrospinning method in accordance with an embodiment of the inventive concepts.

FIG. 3 is a diagram showing a method of manufacturing a member for a gas sensor using metal oxide semiconductor nanofibers including a hetero nanoparticle catalyst using an electrospinning method in accordance with an embodiment of the inventive concepts.

A first process S310 shows an example of performing the electrospinning process on the complex spinning solution 310 including the metal precursor (e.g., tungsten precursor of FIG. 3), the polymer, and the apo-ferritins including the hetero nanoparticle catalysts provided in the hollow regions thereof. At this time, FIG. 3 shows the apo-ferritins 330 including the hetero nanoparticle catalysts which are uniformly distributed in the metal precursor/polymer complex nanofibers 320 manufactured by performing the electrospinning process on the complex spinning solution 310.

A second process S320 shows an example of performing a high-temperature thermal treatment process on the metal precursor/polymer complex nanofibers 320. At this time, since the thermal treatment process is performed on the metal precursor/polymer complex nanofibers 320, the polymer and the protein corresponding to shells of the apo-ferritins 330 including the hetero nanoparticle catalysts may be pyrolyzed to be removed, and metal oxide semiconductor nanofibers 350 including hetero nanoparticle catalysts 340 and 341 may be manufactured as shown in FIG. 3. The hetero nanoparticle catalysts 340 and 341 may be fastened to the surface and the inside of the metal oxide semiconductor nanofibers 350. The metal oxide semiconductor nanofibers 350 may constitute the member 100 for a gas sensor.

In the embodiment of FIG. 3, a tungsten oxide nano complex is manufactured using the tungsten precursor. However, the inventive concepts are not limited thereto. The metal precursor may include any precursor including one of the various metal salts described above.

As described above, the hetero nanoparticle catalyst which has both the chemical sensitization effect and the electronic sensitization effect unlike a conventional catalyst may be uniformly distributed in the one-dimensional nanostructure having a wide surface area without aggregation by the method of manufacturing the member 100 for a gas sensor using the metal oxide semiconductor nanofibers 110 including the hetero nanoparticle catalyst 120 using the electrospinning process in accordance with embodiments of the inventive concepts. As a result, sensitivity of a gas sensor using the member 100 may be greatly improved.

Hereinafter, the inventive concepts will be described in detail through embodiments and comparison examples. The embodiments and the comparison examples are provided only to explain the inventive concepts and are not intended to limit the inventive concepts.

Hereinafter, the inventive concepts will be described in more detail through the embodiments. However, the following embodiments are provided only to explain the inventive concepts in more detail and are not intended to limit the inventive concepts.

First Embodiment: Manufacture of Hetero Pt—Pd, Pt—Rh and Pt—Y Nanoparticle Catalysts Obtained from Apo-Ferritins The following manufacturing processes are performed to form Pt—Pd, Pt—Rh and Pt—Y hetero nanoparticle catalysts into the apo-ferritins.

To embed the metal salt into the hollow inside of the apo-ferritin by the chemical method, a pH of a 1 ml solution (Sigma Aldrich) in which the apo-ferritins of 35 mg/ml are dispersed in a 0.15 M NaCl water solution is adjusted using sodium hydroxide (NaOH) to 8.6, thereby making a condition that the metal salt comes into the apo-ferritins.

To synthesize the hetero nanoparticle catalyst of Pt—Pd, $K_2PtCl_4$ (Sigma Aldrich) of 6 mg and $K_2PdCl_4$ (Sigma Aldrich) of 6 mg are dissolved in 1 ml water to manufacture a Pt—Pd mixture water solution.

To synthesize the hetero nanoparticle catalyst of Pt—Rh, $K_2PtCl_4$ (Sigma Aldrich) of 6 mg and $RhCl_3xH_2O$ (Sigma Aldrich) of 6 mg are dissolved in 1 ml water to manufacture a Pt—Rh mixture water solution.

To synthesize the hetero nanoparticle catalyst of Pt—Y, $K_2PtCl_4$ (Sigma Aldrich) of 5.6 mg and $Y(NO_3)_3 \cdot 6H_2O$ (Sigma Aldrich) of 3.7 mg are dissolved in 1 ml water to manufacture a Pt—Y mixture water solution.

The apo-ferritin water solution having the pH of 8.6 is put in three vials. The Pt—Pd, Pt—Rh and Pt—Y mixture water solutions manufactured above are stirred into the three vials, respectively, while slowly dropping the Pt—Pd, Pt—Rh and Pt—Y mixture water solutions, so Pt/Pd, Pt/Rh and Pt/Y salts may be injected into the hollow regions of the apo-ferritins so as to be embedded in the hollow regions. The stirring process is performed at 100 rpm for one hour at a room temperature.

Next, a 0.5 ml solution including a $NaBH_4$ of 40 mM is added to reduce the hetero salts provided in the hollow regions of the apo-ferritins, so the Pt/Pd, Pt/Rh and Pt/Y salts are reduced to Pt—Pd, Pt—Rh and Pt—Y metal nanoparticles in the apo-ferritins.

Since the water solutions in which the hetero nanoparticle catalysts synthesized using the apo-ferritins are dispersed contain a great amount of the reductant and a great numbers of ligands included in the metal salts, the apo-ferritins including the synthesized hetero nanoparticle catalysts are extracted and several kinds of salt ions (e.g., Cl, Na, and B) dissolved in the water solutions are removed by a centrifugal machine. The centrifugal machine in which each of the water solutions was put was operated at 12000 rpm for ten minutes. The apo-ferritins including the hetero nanoparticles which are extracted by the centrifugal machine are dispersed in water again to manufacture final water solutions in which the apo-ferritins including Pt—Pd, Pt—Rh and Pt—Y nanoparticles therein are dispersed.

Figure 4:
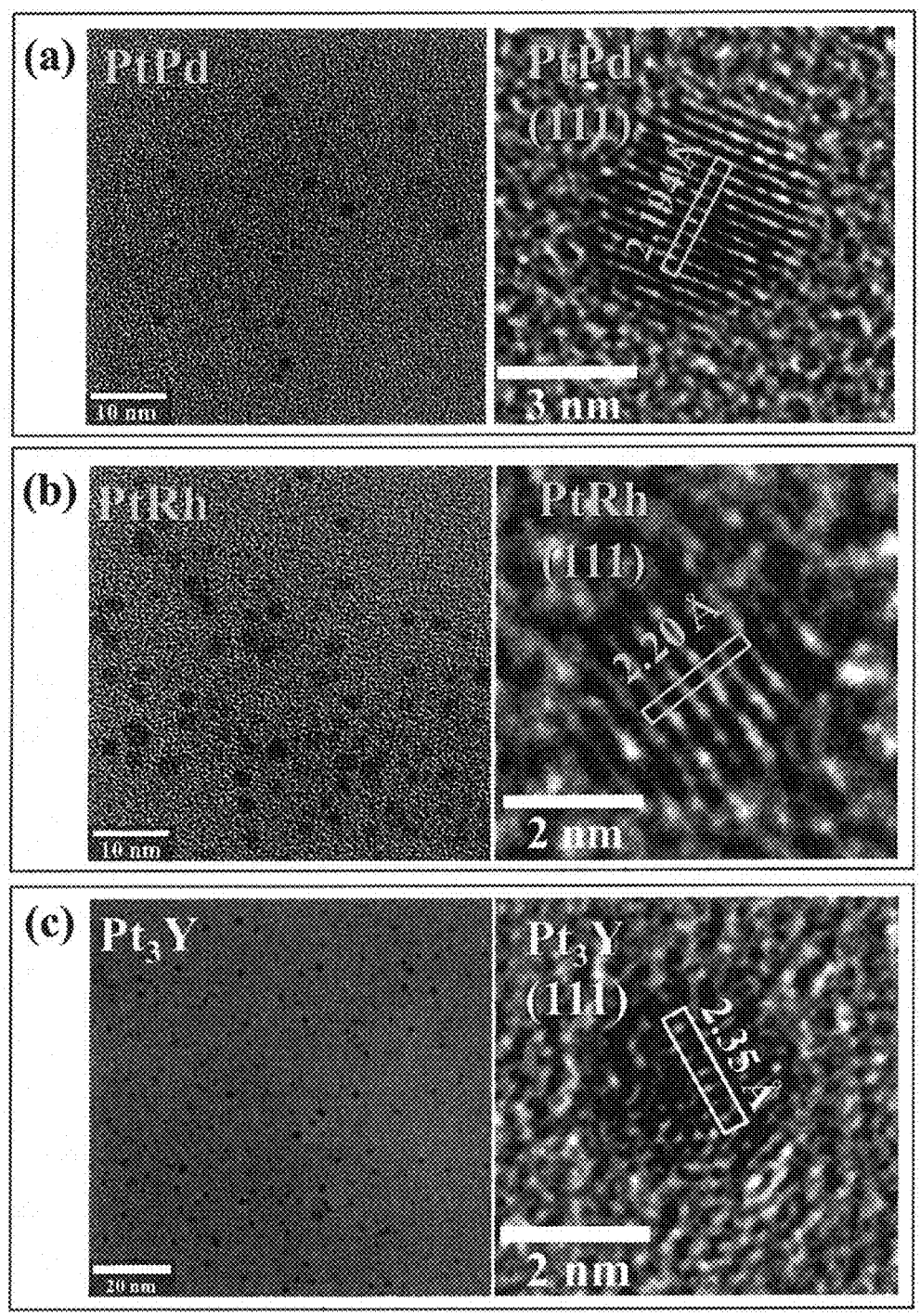
FIG. 4 show transmission electron microscope (TEM) images of a hetero nanoparticle catalyst including platinum and palladium combined with each other (a), a hetero nanoparticle catalyst including platinum and rhodium combined with each other (b), and a hetero nanoparticle catalyst including platinum and yttrium combined with each other (c) which are synthesized using the apo-ferritin in accordance with an embodiment of the inventive concepts.

FIG. 4 show transmission electron microscope (TEM) images of the apo-ferritin 330 including the Pt—Pd nanoparticle catalyst (a), the apo-ferritin 330 including the Pt—Rh nanoparticle catalyst (b) and the apo-ferritin 330 including the Pt—Y nanoparticle catalyst (c). The apo-ferritins including the synthesized hetero (Pt—Pd, Pt—Rh and Pt—Y) nanoparticle catalysts have sphere shapes and have uniform average diameters ranging from 2 nm to 4 nm. The proteins surrounding the hetero nanoparticle catalysts were decomposed by an electronic beam during TEM analysis, so the proteins were not observed.

Second Embodiment: Manufacture of Tungsten Oxide ($WO_3$) Nanofibers (e.g., Metal Oxide Semiconductor Nanofibers 350 of FIG. 3) Including Hetero Pt—Pd Nanoparticle Catalyst After 0.35 g ammonium metatungstate hydrate corresponding to the tungsten precursor is dissolved in 3 ml water at a room temperature, a 30 mg apo-ferritin water solution including the apo-ferritins including the Pt—Pd nanoparticle catalysts manufactured in the first embodiment is added into the 3 ml water including the ammonium metatungstate hydrate to mix the apo-ferritins with a precursor salt. Polyvinylpyrrolidone (PVP; weight-average molecular weight: 1,300,000 g/mol) of 0.5 g for increasing a viscosity of a spinning solution is stirred into the solution, in which the apo-ferritins including the Pt—Pd nanoparticle catalysts and the tungsten precursor are very uniformly dispersed, at a room temperature for 24 hours at 500 rpm, thereby manufacturing the spinning solution.

To perform the electrospinning process, a tungsten precursor/polymer complex spinning solution provided with the apo-ferritins 330 including the Pt—Pd nanoparticle catalyst was put into a syringe, and the syringe was connected to a syringe pump (Henke-Sass Wolf, 10 mL NORM-JECT®) to discharge the complex spinning solution at a discharging rate of 0.5 ml/min. The complex spinning solution was discharged through a needle (27-gauge) of the syringe. A voltage of 16 kV was applied between the needle (27-gauge) and a collector obtaining a nanofiber web. A stainless steel plate (SUS, 0.5 T) was used as the collector of the nanofibers, and a distance between the needle and the collector was 13 cm. During the electrospinning process, the water corresponding to the solvent was evaporated to obtain solidified complex nanofibers 320 in which the tungsten salt precursor, the polyvinylpyrrolidone polymer and the apo-ferritins including the Pt—Pd nanoparticle catalysts were uniformly mixed with each other. The electrospinning process was sufficiently performed for one hour or more to collect the complex nanofibers (e.g., the complex nanofibers 320 of FIG. 3) having a web shape on the collector.

Figure 5:
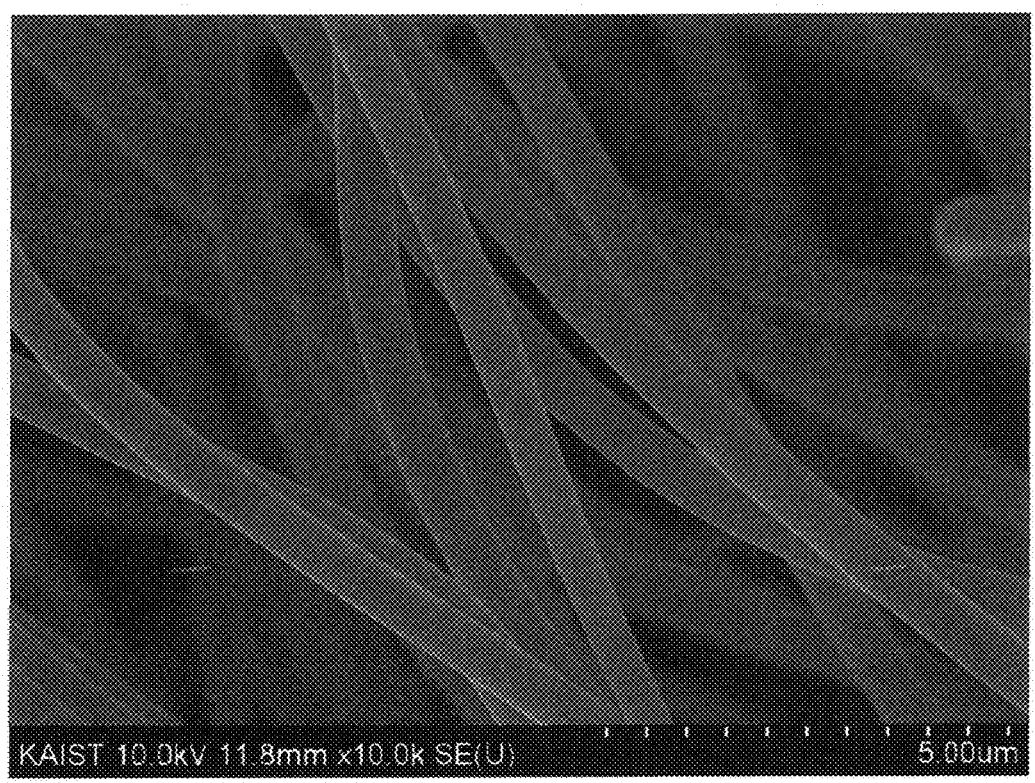
FIG. 5 is a TEM image showing nanofibers obtained by electrospinning the apo-ferritin including the platinum/palladium hetero nanoparticle catalyst in accordance with an embodiment of the inventive concepts and tungsten precursor/polyvinylpyrrolidone (PVP) complex spinning solution before a high-temperature thermal treatment process.

FIG. 5 is a TEM image showing the solidified complex nanofibers, in which the tungsten salt precursor, the polyvinylpyrrolidone polymer and the apo-ferritins including the Pt—Pd nanoparticle catalysts are uniformly mixed with each other, obtained after the electrospinning process. As shown in FIG. 5, the complex nanofibers having a one-dimensional structure, a smooth surface and a diameter of 600 nm to 700 nm is formed by the electrospinning process.

Next, the complex nanofibers manufactured by the processes described above was thermally treated in the air atmosphere. During the thermal treatment process, the complex nanofibers was heated to 600 degrees Celsius at a heating rate of 4° C./min in the air atmosphere in the Vulcan 3-550 small electronic furnace of Ney Co. and was then maintained at 600 degrees Celsius for one hour. Next, the complex nanofibers was cooled to a room temperature at a cooling rate of 4° C./min. At this time, in the tungsten precursor/polyvinylpyrrolidone polymer complex nanofibers including the apo-ferritins including the Pt—Pd nanoparticle catalysts, the polyvinylpyrrolidone polymer maintaining the one-dimensional shape was pyrolyzed to be removed, and the tungsten salt precursor provided therein was oxidized to form tungsten oxide. A pyrolysis temperature of the polyvinylpyrrolidone polymer is in a range of 400 degrees Celsius to 450 degrees Celsius. In addition, the protein shells (pyrolysis temperature: 70 degrees Celsius) of the apo-ferritins including the Pt—Pd nanoparticle catalysts embedded in the complex nanofibers were also pyrolyzed to be removed, and the Pt—Pd nanoparticle catalysts embedded in the protein shells were uniformly fastened within the tungsten oxide nanofibers.

Figure 6:
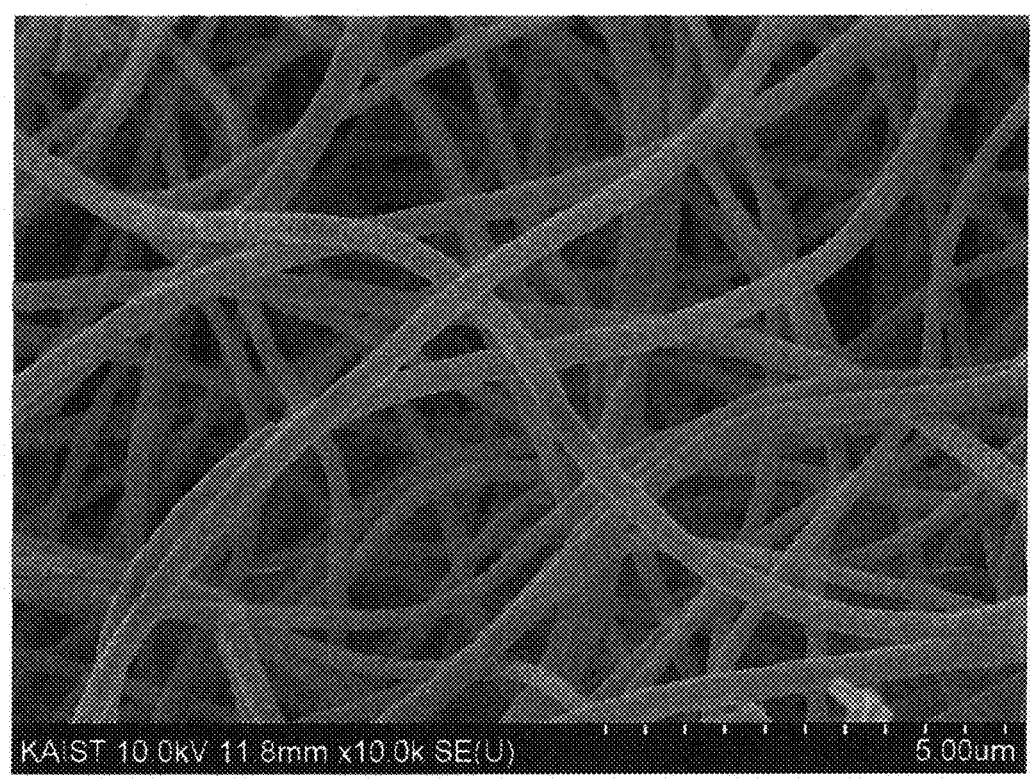
FIG. 6 is a TEM image showing nanofibers obtained after a high-temperature thermal treatment process is performed on tungsten precursor/polyvinylpyrrolidone (PVP) complex nanofibers including the apo-ferritin including the platinum/palladium hetero nanoparticle catalyst in accordance with an embodiment of the inventive concepts.

FIG. 6 is a TEM image showing the tungsten oxide semiconductor nanofibers (e.g., the metal oxide semiconductor nanofibers 350 of FIG. 3) including the Pt—Pd nanoparticle catalyst (e.g., the hetero nanoparticle catalyst 121 of FIG. 1 or the hetero nanoparticle catalyst 341 of FIG. 3) obtained after the thermal treatment process in the second embodiment. The tungsten oxide semiconductor nanofibers including the Pt—Pd nanoparticle catalyst has a one-dimensional metal oxide shape by the removal of the polyvinylpyrrolidone polymer and is shrunk poly-crystalline oxide nanofibers having a diameter of 400 nm to 500 nm, unlike the nanofibers before the thermal treatment process.

Third Embodiment: Manufacture of Tungsten Oxide ($WO_3$) Nanofibers (e.g., Metal Oxide Semiconductor Nanofibers 350 of FIG. 3) Including Hetero Pt—Rh Nanoparticle Catalyst The manufactured apo-ferritins including the Pt—Rh nanoparticle catalysts were mixed with the tungsten precursor and the polyvinylpyrrolidone polymer under the same conditions as those of the second embodiment to make a spinning solution, and tungsten oxide nanofibers including the Pt—Rh nanoparticle catalyst were synthesized by performing the same thermal treatment process as described in the second embodiment on the spinning solution of the present embodiment.

Figure 7:
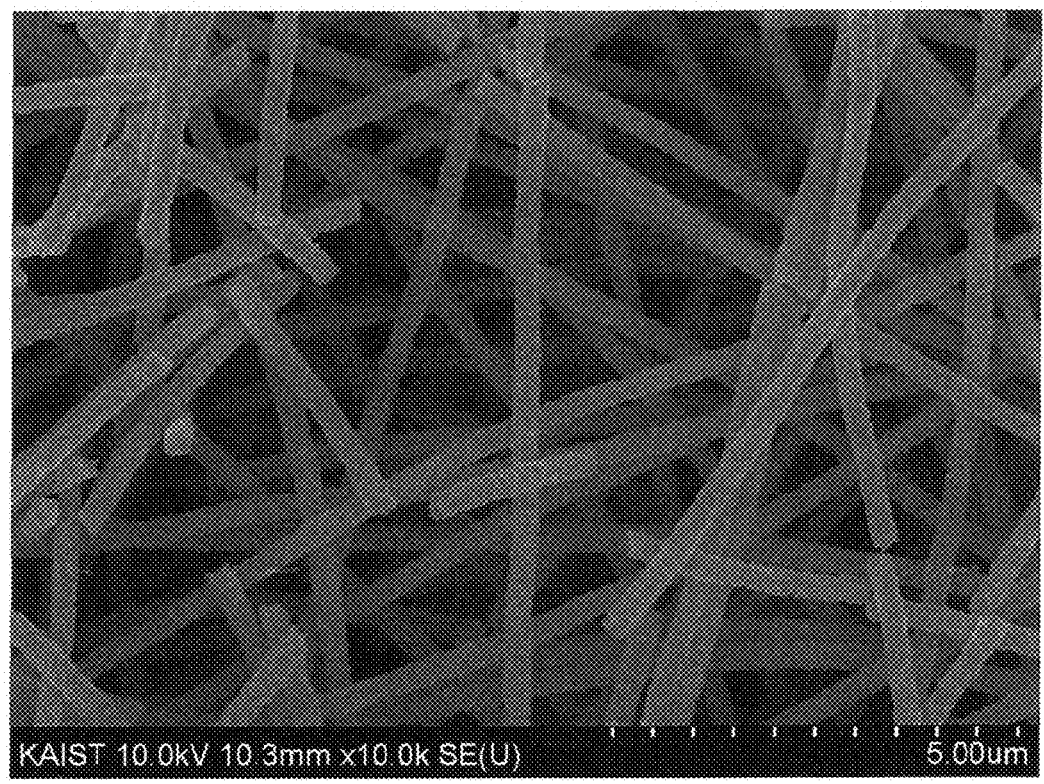
FIG. 7 is a TEM image showing nanofibers obtained after a high-temperature thermal treatment process is performed on tungsten precursor/polyvinylpyrrolidone (PVP) complex nanofibers including the apo-ferritin including the platinum/rhodium hetero nanoparticle catalyst in accordance with an embodiment of the inventive concepts.

FIG. 7 is a TEM image showing the tungsten oxide semiconductor nanofibers (e.g., the metal oxide semiconductor nanofibers 350 of FIG. 3) including the Pt—Rh nanoparticle catalyst (e.g., the hetero nanoparticle catalyst 121 of FIG. 1 or the hetero nanoparticle catalyst 341 of FIG. 3) obtained after the thermal treatment process in the third embodiment. The tungsten oxide semiconductor nanofibers including the Pt—Rh nanoparticle catalyst has a one-dimensional metal oxide shape by the removal of the polyvinylpyrrolidone polymer and has the same diameter and shape as the tungsten oxide semiconductor nanofibers including the Pt—Pd nanoparticle catalyst of FIG. 6.

Fourth Embodiment: Manufacture of Tungsten Oxide ($WO_3$) Nanofibers (e.g., Metal Oxide Semiconductor Nanofibers 350 of FIG. 3) Including Hetero Pt—Y Nanoparticle Catalyst The manufactured apo-ferritins including the Pt—Y nanoparticle catalysts were mixed with the tungsten precursor and the polyvinylpyrrolidone polymer under the same conditions as those of the second embodiment to make a spinning solution, and a tungsten oxide nanofibers including the Pt—Y nanoparticle catalyst was synthesized by performing the same thermal treatment process as described in the second embodiment on the spinning solution of the present embodiment.

Figure 8:
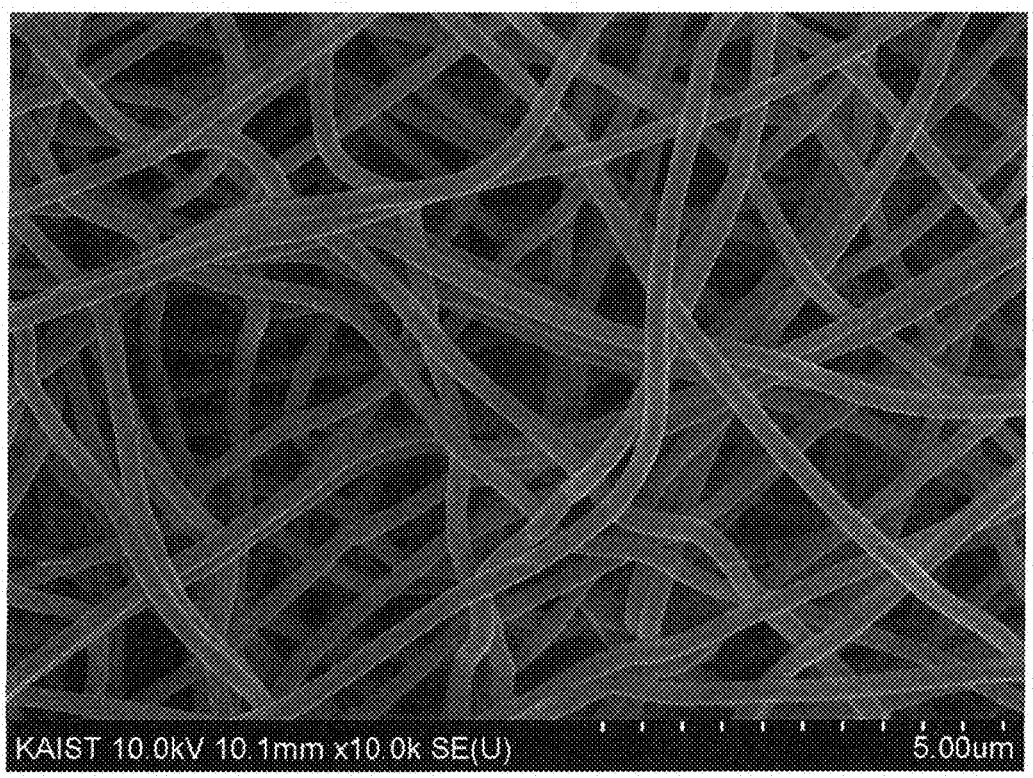
FIG. 8 is a TEM image showing nanofibers obtained after a high-temperature thermal treatment process is performed on tungsten precursor/polyvinylpyrrolidone (PVP) complex nanofibers including the apo-ferritin including the platinum/yttrium hetero nanoparticle catalyst in accordance with an embodiment of the inventive concepts.

FIG. 8 is a TEM image showing the tungsten oxide semiconductor nanofibers (e.g., the metal oxide semiconductor nanofibers 350 of FIG. 3) including the Pt—Y nanoparticle catalyst (e.g., the hetero nanoparticle catalyst 121 of FIG. 1 or the hetero nanoparticle catalyst 341 of FIG. 3) obtained after the thermal treatment process in the fourth embodiment. The tungsten oxide semiconductor nanofibers including the Pt—Y nanoparticle catalyst has a one-dimensional metal oxide shape by the removal of the polyvinylpyrrolidone polymer and has the same diameter and shape as the tungsten oxide semiconductor nanofibers including the Pt—Pd nanoparticle catalyst of FIG. 6.

First Comparison Example: Manufacture of Tungsten Oxide Nanofibers Including Mono Pt Nanoparticle Catalyst Obtained from Apo-Ferritin Tungsten oxide nanofibers containing mono Pt nanoparticle catalysts obtained from apo-ferritins were manufactured in order to be compared with the tungsten oxide nanofibers including the Pt—Pd nanoparticles obtained from the apo-ferritins including the hetero nanoparticle catalysts (e.g., the hetero nanoparticle catalyst 121 of FIG. 1) manufactured in the second embodiment.

The same method as described in the first embodiment was performed to manufacture the mono Pt nanoparticle catalyst using the apo-ferritin except for a source for synthesizing nanoparticle catalysts. In other word, $K_2PtCl_4$ and $K_2PdCl_4$ were used to synthesize the hetero Pt—Pd nanoparticle catalyst in the first embodiment, but a 20 mg/ml solution using $H_2PtCl_6.H_2O$ was prepared and applied in order to synthesize the mono Pt nanoparticle catalysts using the apo-ferritins.

Figure 9:
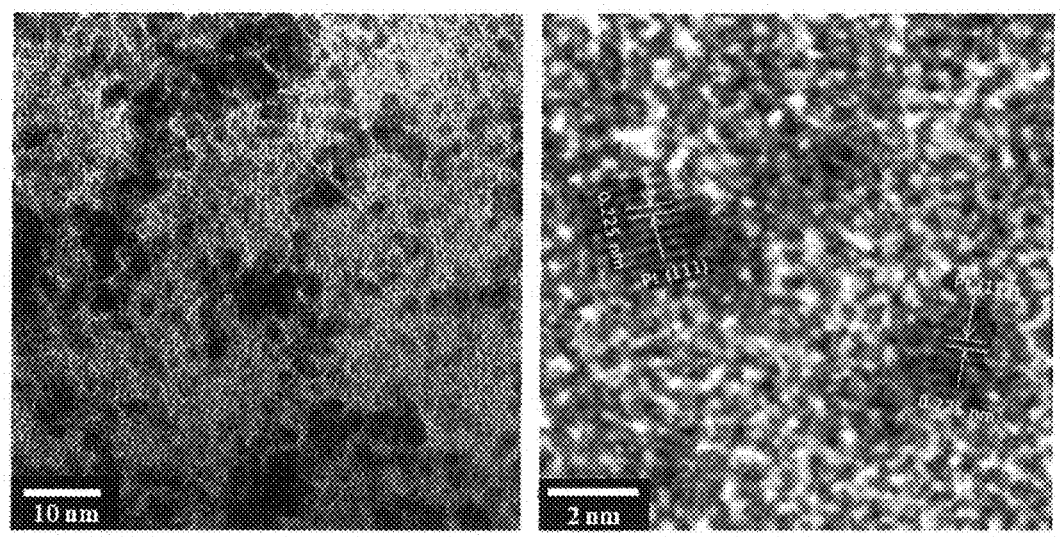
FIG. 9 is a TEM image showing an apo-ferritin including a platinum nanoparticle catalyst according to a first comparison example.

FIG. 9 is a TEM image showing the apo-ferritin including the Pt nanoparticle catalyst, manufactured by the above processes. The synthesized apo-ferritins including the Pt nanoparticle catalysts have sphere shapes like the apo-ferritins including the hetero Pt—Pd nanoparticle catalysts and have a little small average diameter of 1 nm to 2 nm. A size of the nanoparticle formed in the hollow region of the apo-ferritin may be adjusted by adjusting a content of a metal salt and a process parameter.

The manufactured apo-ferritins including the Pt nanoparticle catalysts were mixed with the tungsten precursor and the polyvinylpyrrolidone polymer under the same conditions as those of the second embodiment to make a spinning solution, and tungsten oxide nanofibers including the Pt nanoparticle catalysts was synthesized by performing the same thermal treatment process as described in the second embodiment on the spinning solution of the present comparison example.

Figure 10:
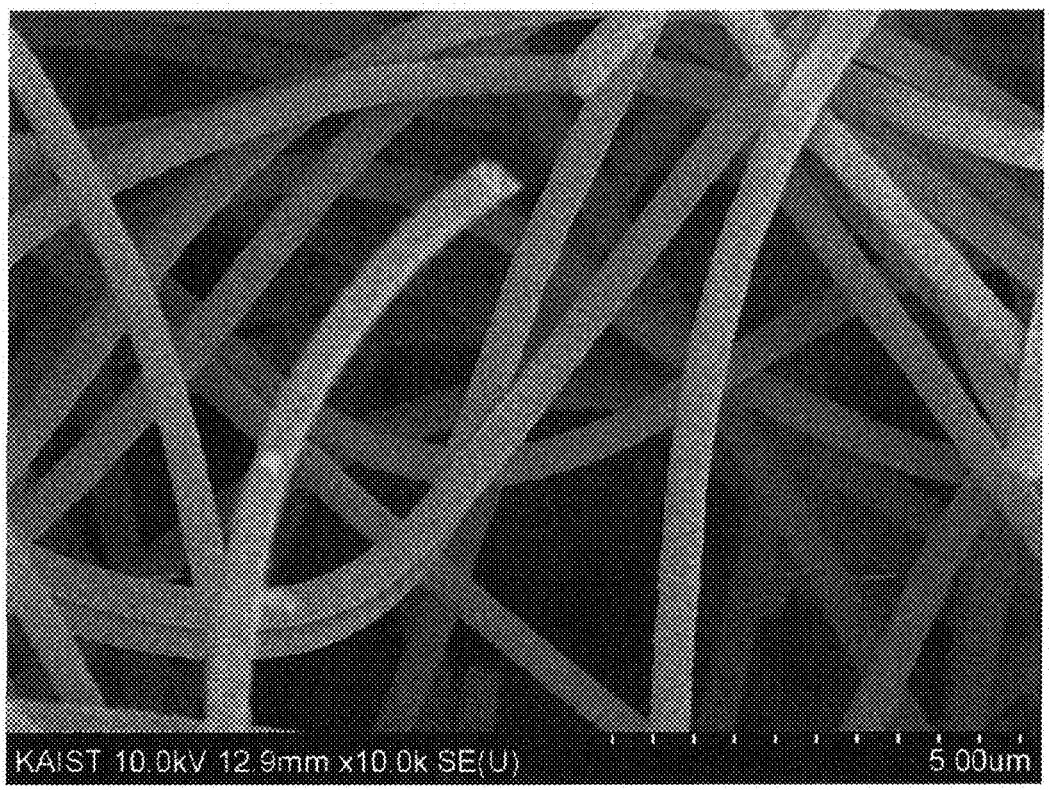
FIG. 10 is a TEM image showing nanofibers obtained after a high-temperature thermal treatment process is performed on tungsten precursor/polyvinylpyrrolidone (PVP) complex nanofibers including the apo-ferritin including the platinum nanoparticle catalyst according to the first comparison example.

FIG. 10 is a TEM image showing the tungsten oxide nanofibers including the mono Pt nanoparticle catalysts, which is obtained by performing an electrospinning process using the spinning solution including the apo-ferritins including the mono Pt nanoparticle catalysts, the tungsten precursor and the polyvinylpyrrolidone polymer and by performing the same thermal treatment process as described in the second embodiment. As shown in FIG. 10, the tungsten oxide nanofibers including the mono Pt nanoparticle catalysts has the same diameter and shape as the tungsten oxide nanofibers including the hetero Pt—Pd nanoparticle catalysts of FIG. 6.

Figure 11:
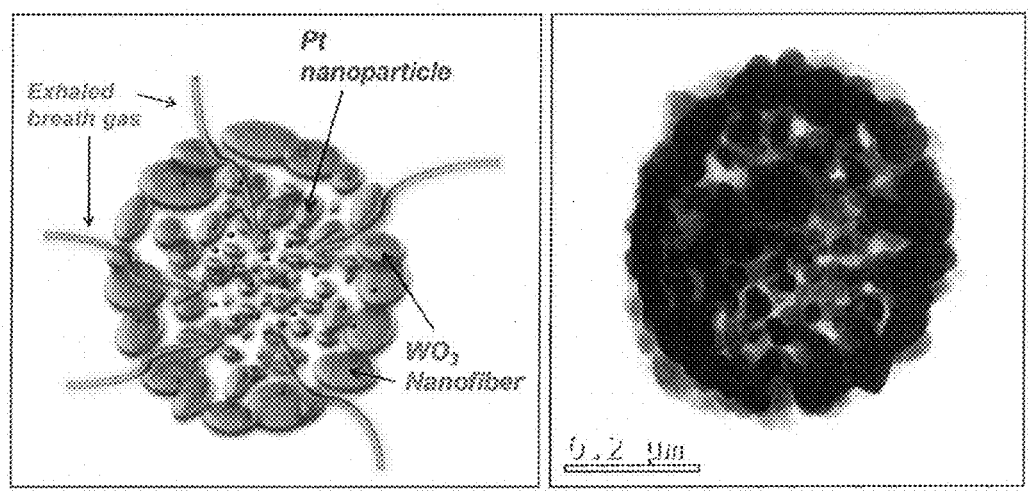
FIG. 11 shows a cross-sectional view and a TEM image, obtained using a focused ion beam (FIB), of a sensing material obtained after the high-temperature thermal treatment process is performed on the tungsten precursor/polyvinylpyrrolidone (PVP) complex nanofiber including the apo-ferritin including the platinum nanoparticle catalyst according to the first comparison example.
Figure 12:
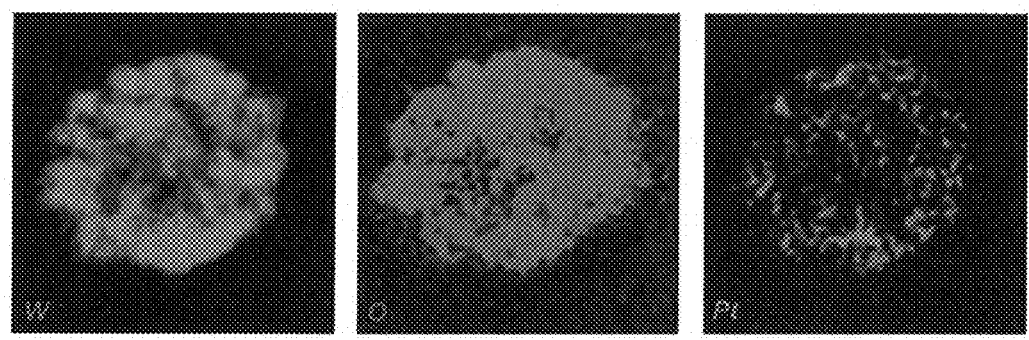
FIG. 12 shows energy dispersive X-ray spectrometer (EDS) images of a TEM, obtained using a FIB, of the sensing material obtained after the high-temperature thermal treatment process is performed on the tungsten oxide precursor/polyvinylpyrrolidone (PVP) complex nanofiber including the apo-ferritin including the platinum nanoparticle catalyst according to the first comparison example.

FIG. 11 shows a cross-sectional view and a TEM image, obtained using a focused ion beam (FIB), of a tungsten oxide nanofiber to which the mono Pt nanoparticle catalysts are fastened. As shown in a cross-sectional view of FIG. 11, if several kinds of gases reach the tungsten oxide nanofiber to which the mono Pt nanoparticle catalysts are fastened, the gases are permeated into the inside of the tungsten oxide nanofiber through pores between outer tungsten oxides of which grains are greatly grown to have great grain sizes, and porous tungsten oxides having small grain sizes are fastened to the Pt nanoparticle catalysts in the inside of the tungsten oxide nanofiber, thereby improving reactivity of the permeated gases. Thus, a high-sensitivity structure is obtained. General known methods of increasing a sensitivity of a metal oxide includes a method of reducing grain sizes of the metal oxide to maximize an electron depletion layer of the metal oxide when a gas is adsorbed, and a method of realizing a porous structure in which catalysts are uniformly distributed. In processes of decomposing and removing apo-ferritin protein and of crystallizing a nanofibers, fine pores having sizes ranging from 0.5 nm to 50 nm may be formed in the metal oxide nanofibers. As shown in the TEM image of FIG. 11, the tungsten oxide nanofiber has a grain size gradient from an outer portion to an inner portion thereof. Thus, the tungsten oxide nanofiber has the structure increasing the reactivity of the gases. FIG. 12 shows images obtained by performing element-component analysis on the tungsten oxide nanofiber including the mono Pt nanoparticle catalyst of FIG. 11 by an energy dispersive X-ray spectrometer (EDS). As shown in FIG. 12, tungsten (W, expressed by a red color) and oxygen (O, expressed by a green color) constituting the tungsten oxide were detected, and platinum (Pt) synthesized using the apo-ferritin and contained in the nanofiber was uniformly detected in the nanofiber.

Figure 13:
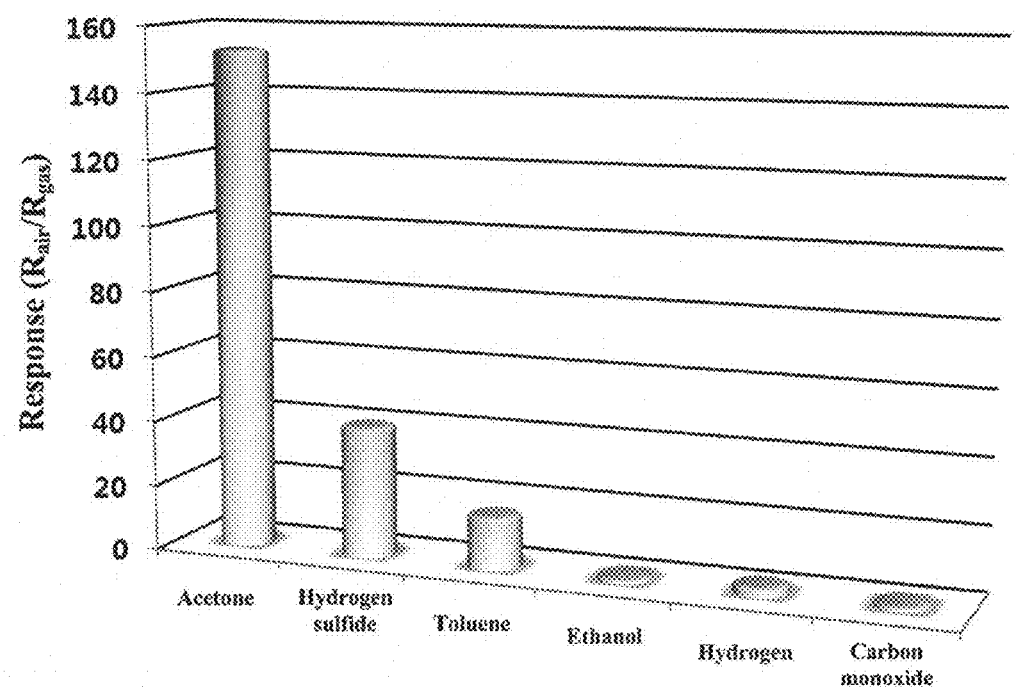
FIG. 13 is a graph showing responses of the nanofiber sensing material, containing the platinum nanoparticle catalyst according to the first comparison example, to an acetone gas of 5 ppm, a hydrogen sulfide gas of 5 ppm, a toluene gas of 5 ppm, an ethanol gas of 5 ppm, a hydrogen gas of 5 ppm, and a carbon monoxide gas of 5 ppm.

FIG. 13 is a graph showing characteristic evaluation of a gas sensor using the tungsten oxide nanofibers to which the mono Pt nanoparticle catalysts are fastened. A manufacturing method of the gas sensor was the same as a manufacturing method to be described below in a first experimental example. Response characteristics of the gas sensor to an acetone ($CH_3COCH_3$) gas of 5 ppm, a hydrogen sulfide ($H_2S$) gas of 5 ppm, a toluene ($C_6H_5CH_3$) gas of 5 ppm, an ethanol ($C_2H_5OH$) gas of 5 ppm, a hydrogen ($H_2$) gas of 5 ppm and a carbon monoxide (CO) gas of 5 ppm were evaluated in relative humidity of 85% RH to 95% RH similar to humidity of gases coming from mouths of men under a condition that a driving temperature of the gas sensor was 350 degrees Celsius. As a result of the evaluation, the response ($R_{air}/R_{gas}$) of the tungsten oxide nanofibers including the mono Pt nanoparticle catalysts to acetone was 153, so the tungsten oxide nanofibers including the mono Pt nanoparticle catalysts very selectively responded to the acetone gas.

Second Comparison Example: Manufacture of Tungsten Oxide Nanofibers Including Mono Pd Nanoparticle Catalyst Obtained from Apo-Ferritin Tungsten oxide nanofibers containing mono Pd nanoparticle catalysts obtained from apo-ferritins was manufactured in order to be compared with the tungsten oxide nanofibers including the Pt—Pd nanoparticles obtained from the apo-ferritins including the hetero nanoparticle catalysts (e.g., the hetero nanoparticle catalyst 121 of FIG. 1) manufactured in the second embodiment.

The same method as described in the first embodiment was performed to manufacture the mono Pt nanoparticle catalysts using the apo-ferritins except for a source for synthesizing the nanoparticle catalysts. In other word, $K_2PtCl_4$ and $K_2PdCl_4$ were used to synthesize the hetero Pt—Pd nanoparticle catalysts in the first embodiment, but a 10 mg/ml solution using $K_2PdCl_4$ was prepared and applied in order to synthesize the mono Pd nanoparticle catalysts using the apo-ferritins.

Figure 14:
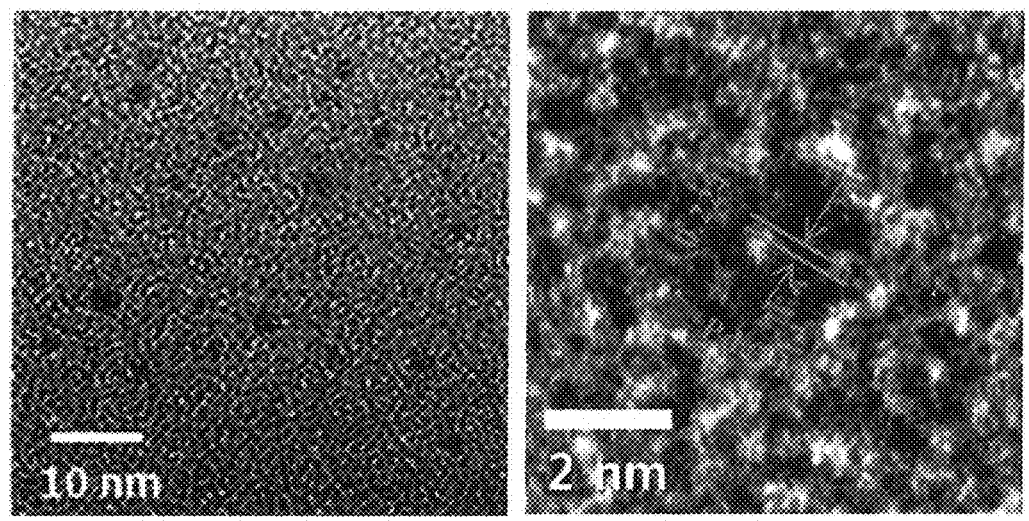
FIG. 14 is a TEM image showing an apo-ferritin including a palladium nanoparticle catalyst according to a second comparison example.

FIG. 14 is a TEM image showing the apo-ferritin including the palladium nanoparticle catalyst obtained in the second comparison example. The synthesized apo-ferritins including the Pd nanoparticle catalysts have sphere shapes like the apo-ferritins including the hetero Pt—Pd nanoparticle catalysts and have a little small average diameter of 1 nm to 2 nm.

The manufactured apo-ferritins including the Pd nanoparticle catalysts were mixed with the tungsten precursor and the polyvinylpyrrolidone polymer under the same conditions as those of the second embodiment to make a spinning solution, and tungsten oxide nanofibers including the Pd nanoparticle catalysts was synthesized by performing the same thermal treatment process as described in the second embodiment on the spinning solution of the present comparison example.

Figure 15:
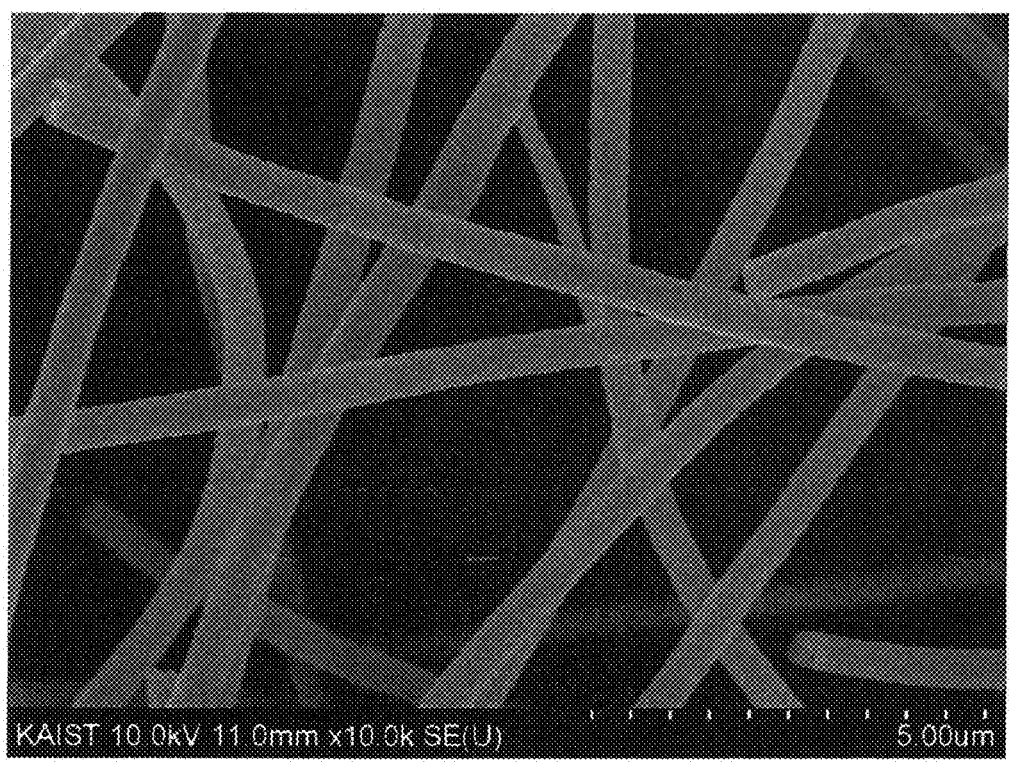
FIG. 15 is a TEM image showing nanofibers obtained after a high-temperature thermal treatment process is performed on tungsten precursor/polyvinylpyrrolidone (PVP) complex nanofibers including the apo-ferritin including the palladium nanoparticle catalyst according to the first comparison example.

FIG. 15 is a TEM image showing the tungsten oxide nanofibers including the mono Pd nanoparticle catalysts, which is obtained by performing an electrospinning process using the spinning solution including the apo-ferritins including the mono Pd nanoparticle catalysts, the tungsten precursor and the polyvinylpyrrolidone polymer and by performing the same thermal treatment process as described in the second embodiment. As shown in FIG. 15, the tungsten oxide nanofibers including the mono Pd nanoparticle catalysts has the same diameter and shape as the tungsten oxide nanofibers including the hetero Pt—Pd nanoparticle catalysts of FIG. 6.

Figure 16:
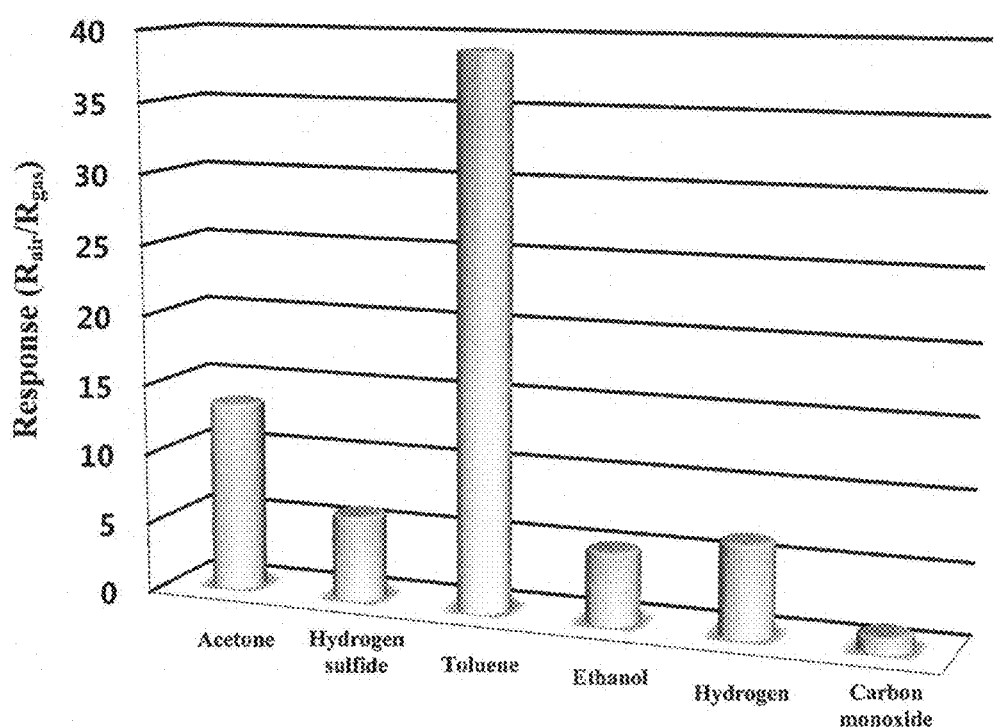
FIG. 16 is a graph showing responses of nanofiber sensing material, containing the palladium nanoparticle catalyst according to the second comparison example, to an acetone gas of 5 ppm, a hydrogen sulfide gas of 5 ppm, a toluene gas of 5 ppm, an ethanol gas of 5 ppm, a hydrogen gas of 5 ppm, and a carbon monoxide gas of 5 ppm.

FIG. 16 is a graph showing characteristic evaluation of a gas sensor using the tungsten oxide nanofibers to which the mono Pd nanoparticle catalysts are fastened. A manufacturing method of the gas sensor was the same as the manufacturing method to be described below in the first experimental example. Response characteristics of the gas sensor to an acetone ($CH_3COCH_3$) gas of 5 ppm, a hydrogen sulfide ($H_2S$) gas of 5 ppm, a toluene ($C_6H_5CH_3$) gas of 5 ppm, an ethanol ($C_2H_5OH$) gas of 5 ppm, a hydrogen ($H_2$) gas of 5 ppm and a carbon monoxide (CO) gas of 5 ppm were evaluated in relative humidity of 85% RH to 95% RH similar to humidity of gases coming from mouths of men under a condition that a driving temperature of the gas sensor was 350 degrees Celsius. As a result of the evaluation, the response ($R_{air}/R_{gas}$) of the tungsten oxide nanofibers including the mono Pd nanoparticle catalysts to toluene was 39, so the tungsten oxide nanofibers including the mono Pd nanoparticle catalysts very selectively responded to the toluene gas.

Gas sensors were manufactured to check gas response characteristics of the tungsten oxide nanofibers including the mono Pt nanoparticle catalysts manufactured in the first comparison example, the tungsten oxide nanofibers including the mono Pd nanoparticle catalysts manufactured in the second comparison example, and the tungsten oxide nanofibers including the hetero Pt—Pd nanoparticle catalysts manufactured in the second embodiment.

First Experimental Example: Manufacture and Characteristic Evaluation of Gas Sensors Including Tungsten Oxide Nanofibers Including Hetero Pt—Pd Nanoparticle Catalysts, Tungsten Oxide Nanofibers Including Mono Pt Nanoparticle Catalysts, and Tungsten Oxide Nanofibers Including Mono Pd Nanoparticle Catalysts, Respectively A sensor for detecting a harmful environment gas and diagnosing exhaled breath was manufactured using the tungsten oxide nanofibers containing the hetero Pt—Pd nanoparticle catalysts manufactured according to the inventive concepts, and characteristics of the sensor were analyzed.

Each of the tungsten oxide nanofiber 110 containing the hetero Pt—Pd nanoparticle catalysts and the tungsten oxide nanofibers containing the mono Pt and Pd nanoparticle catalysts was dispersed in ethanol, and an ultrasonic pulverization process was performed on the ethanol including the nanofibers for 30 minutes to pulverize the nanofibers. Gold (Au) sensor electrodes of a linger shape were formed on an alumina ($Al_2O_3$) substrate having an area of 3 mm×3 mm with distances of 150 μm interposed therebetween. Each of the Au sensor electrodes had a thickness of 25 μm and a length of 345 μm. A sensing material including the manufactured catalyst particles was coated on the substrate having the electrodes by a drop coating method. In the coating method, a 3 μl mixture solution experiencing the ultrasonic pulverization process was dropped and coated on the substrate having the sensor electrodes by a micro pipet, and then, the substrate coated with the mixture solution was dried on a hot plate of 80 degrees Celsius. These processes were repeated four to five times to nicely coat the gas sensing material between the electrodes.

The Au sensor electrodes were formed on a front side of the alumina substrate, and a micro heater was adhered to a back side of the alumina substrate opposite to the front side. A temperature of the alumina substrate was adjusted according to a voltage applied to the micro heater.

A hydrogen sulfide ($H_2S$) gas, an acetone ($CH_3COCH_3$) gas, a toluene ($C_6H_5CH_3$) gas, and an ethanol ($C_2H_5OH$) gas are biomarker gases for diagnosing foul breath, diabetes, lung cancer, and an alcohol index, respectively. To evaluate exhaled breath sensor characteristics, response characteristics of the gas sensor to each of the gases was evaluated at a sensor driving temperature of 350 degrees Celsius in relative humidity of 85% RH to 95% RH similar to humidity of gases coming from mouths of men while changing a concentration of each of the gases in an order of 5 ppm, 4 ppm, 3 ppm, 2 ppm, and 1 ppm.

A resistance value varied when each of the gases flowed was detected using the 34972A model of Agilent Co. and a response ($R_{air}/R_{gas}$ resistance variation) of the sensor to each of the gases was analyzed to check sensitivity characteristics of the sensor. Here, "$R_{air}$" denotes a resistance in air, and "$R_{gas}$" denotes a resistance when the gas flows.

FIGS. 17, 18, 19, and 20 show test results of the gas sensors which include the tungsten oxide nanofibers containing the hetero Pt—Pd nanoparticle catalysts of the second embodiment, the tungsten oxide nanofibers containing the mono Pt nanoparticle catalysts of the first comparison example, and the tungsten oxide nanofibers containing the mono Pd nanoparticle catalysts of the second comparison example, respectively.

Figure 17:
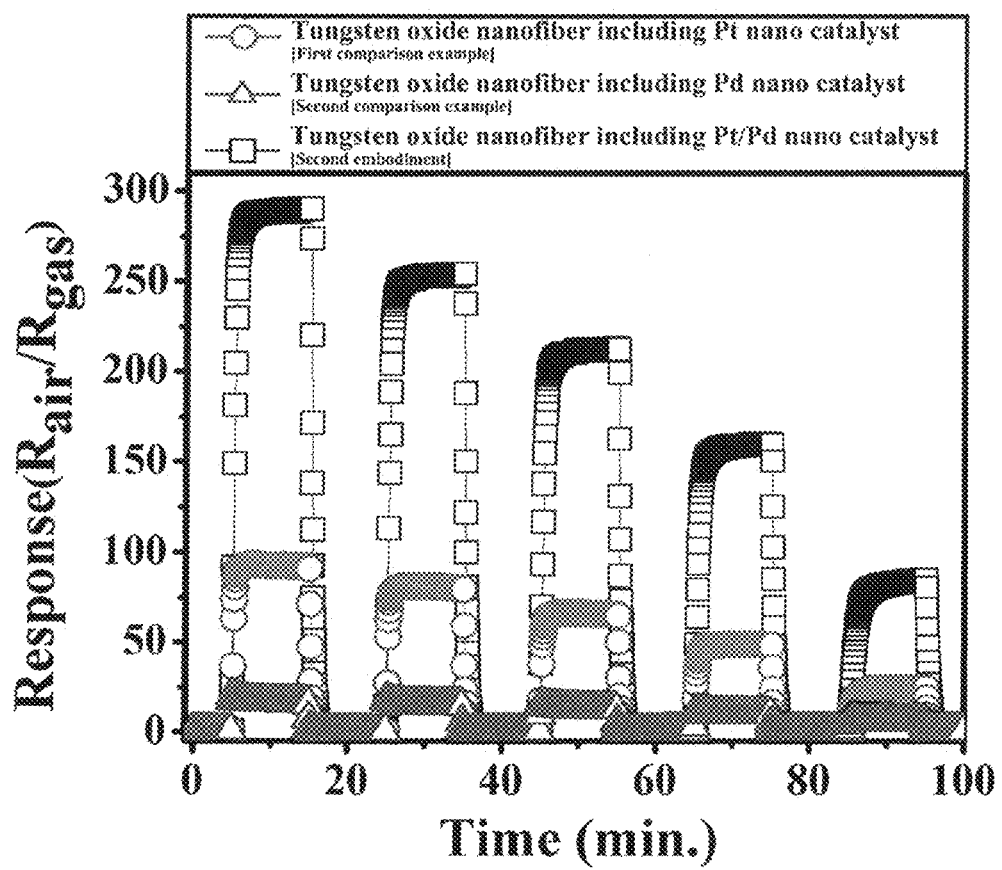
FIG. 17 is a graph showing responses of tungsten oxide nanofibers, which include the hetero platinum/palladium nanoparticle catalyst according to an embodiment of the inventive concepts, the mono platinum nanoparticle catalyst according to the first comparison example and the mono palladium nanoparticle catalyst according to the second comparison example, respectively, to an acetone gas (1 ppm to 5 ppm) at 300 degrees Celsius.

FIG. 17 shows responses ($R_{air}/R_{gas}$) according to a time when the concentration of the acetone gas is reduced in an order of 5 ppm, 4 ppm, 3 ppm, 2 ppm, and 1 ppm at 300 degrees Celsius. Here, "$R_{air}$" denotes a resistance value of the metal oxide material when air is injected, and "$R_{gas}$" denotes a resistance value of the metal oxide material when the acetone gas is injected.

As shown in FIG. 17, the response characteristic of the sensor manufactured using the tungsten oxide nanofibers containing the hetero Pt—Pd nanoparticle catalysts is 3 times higher than that of the sensor manufactured using the tungsten oxide nanofibers containing the mono Pt nanoparticle catalysts and is 16 times higher than that of the sensor manufactured using the tungsten oxide nanofibers containing the mono Pd nanoparticle catalyst at 5 ppm.

Figure 18:
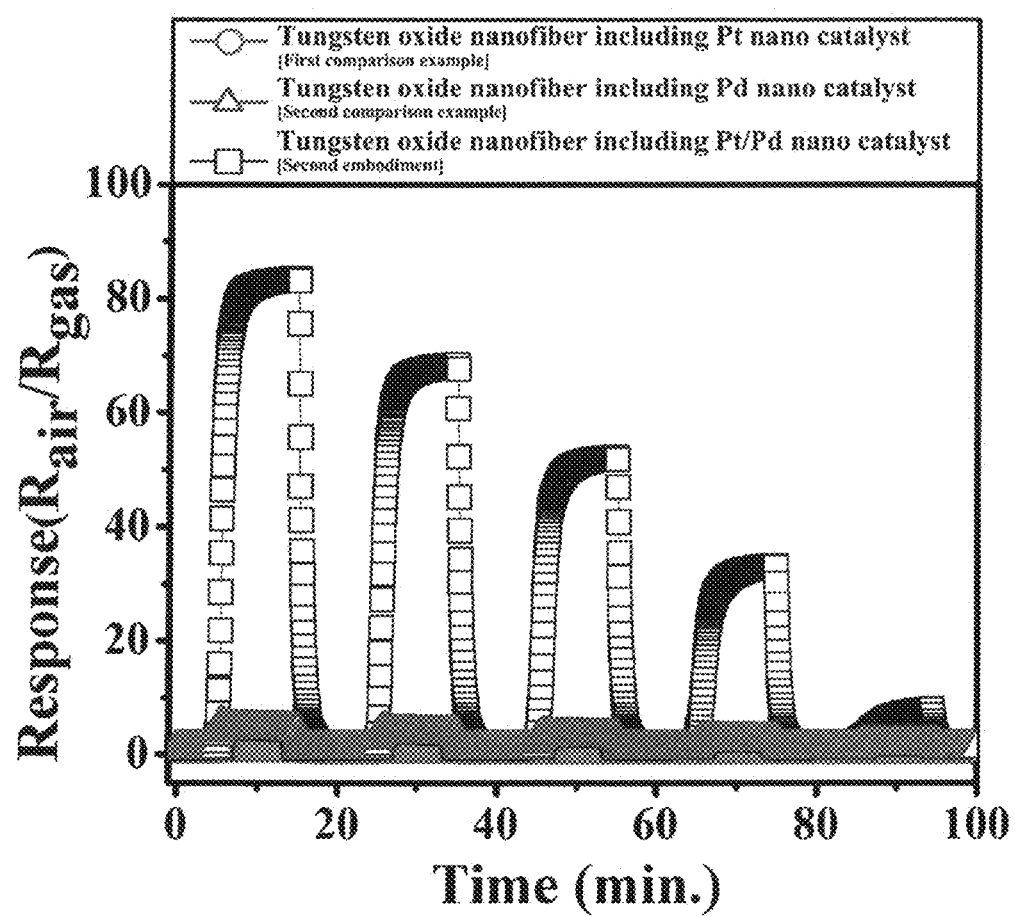
FIG. 18 is a graph showing responses of the tungsten oxide nanofibers, which include the hetero platinum/palladium nanoparticle catalyst according to an embodiment of the inventive concepts, the mono platinum nanoparticle catalyst according to the first comparison example and the mono palladium nanoparticle catalyst according to the second comparison example, respectively, to an ethanol gas (1 ppm to 5 ppm) at 300 degrees Celsius.

FIG. 18 shows responses ($R_{air}/R_{gas}$) according to a time when the concentration of the ethanol gas is reduced in an order of 5 ppm, 4 ppm, 3 ppm, 2 ppm, and 1 ppm at 300 degrees Celsius. Here, "$R_{air}$" denotes a resistance value of the metal oxide material when air is injected, and "$R_{gas}$" denotes a resistance value of the metal oxide material when the ethanol gas is injected.

As shown in FIG. 18, the response characteristic of the sensor manufactured using the tungsten oxide nanofibers containing the hetero Pt—Pd nanoparticle catalysts is 18 times higher than that of the sensor manufactured using the tungsten oxide nanofibers containing the mono Pt nanoparticle catalysts and is 55 times higher than that of the sensor manufactured using the tungsten oxide nanofibers containing the mono Pd nanoparticle catalyst at 5 ppm.

Figure 19:
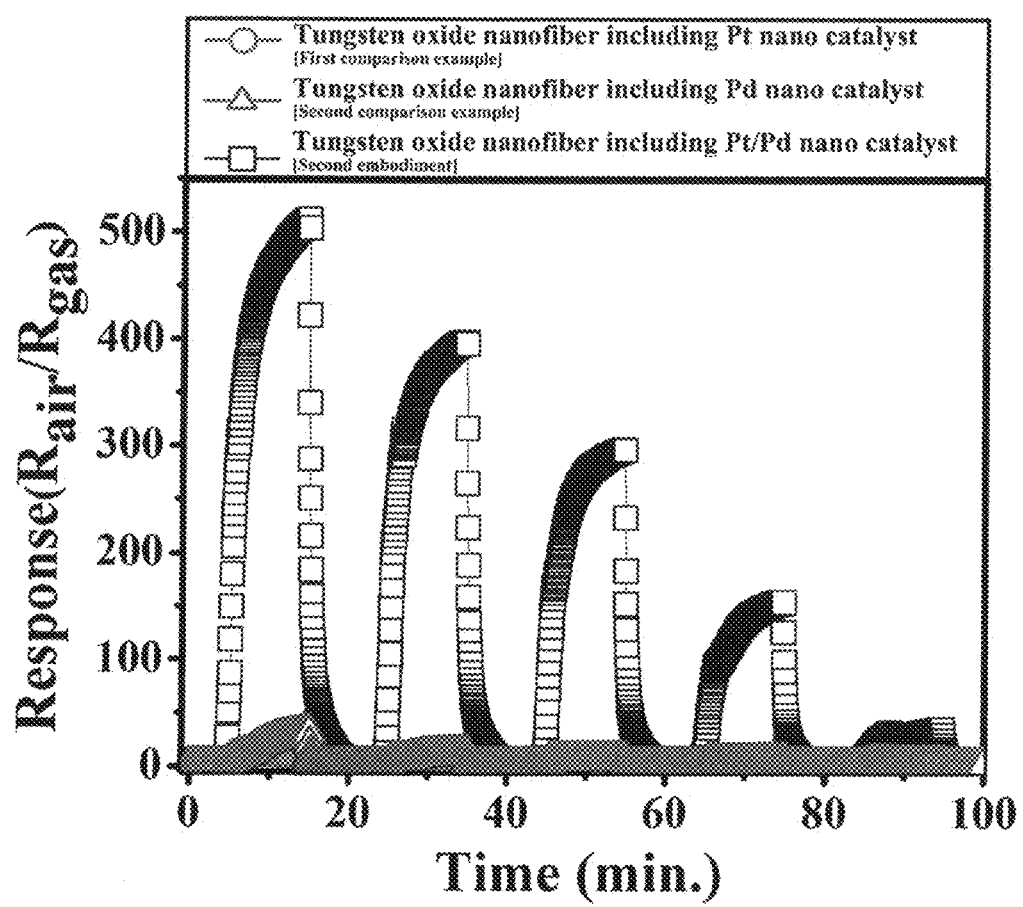
FIG. 19 is a graph showing responses of the tungsten oxide nanofibers, which include the hetero platinum/palladium nanoparticle catalyst according to an embodiment of the inventive concepts, the mono platinum nanoparticle catalyst according to the first comparison example and the mono palladium nanoparticle catalyst according to the second comparison example, respectively, to an hydrogen sulfide gas (1 ppm to 5 ppm) at 300 degrees Celsius.

FIG. 19 shows responses ($R_{air}/R_{gas}$) according to a time when the concentration of the hydrogen sulfide gas is reduced in an order of 5 ppm, 4 ppm, 3 ppm, 2 ppm, and 1 ppm at 300 degrees Celsius. Here, "$R_{air}$" denotes a resistance value of the metal oxide material when air is injected, and "$R_{gas}$" denotes a resistance value of the metal oxide material when the hydrogen sulfide gas is injected.

As shown in FIG. 19, the response characteristic of the sensor manufactured using the tungsten oxide nanofibers containing the hetero Pt—Pd nanoparticle catalysts is 25 times higher than that of the sensor manufactured using the tungsten oxide nanofibers containing the mono Pt nanoparticle catalysts and is 50 times higher than that of the sensor manufactured using the tungsten oxide nanofibers containing the mono Pd nanoparticle catalyst at 5 ppm.

Figure 20:
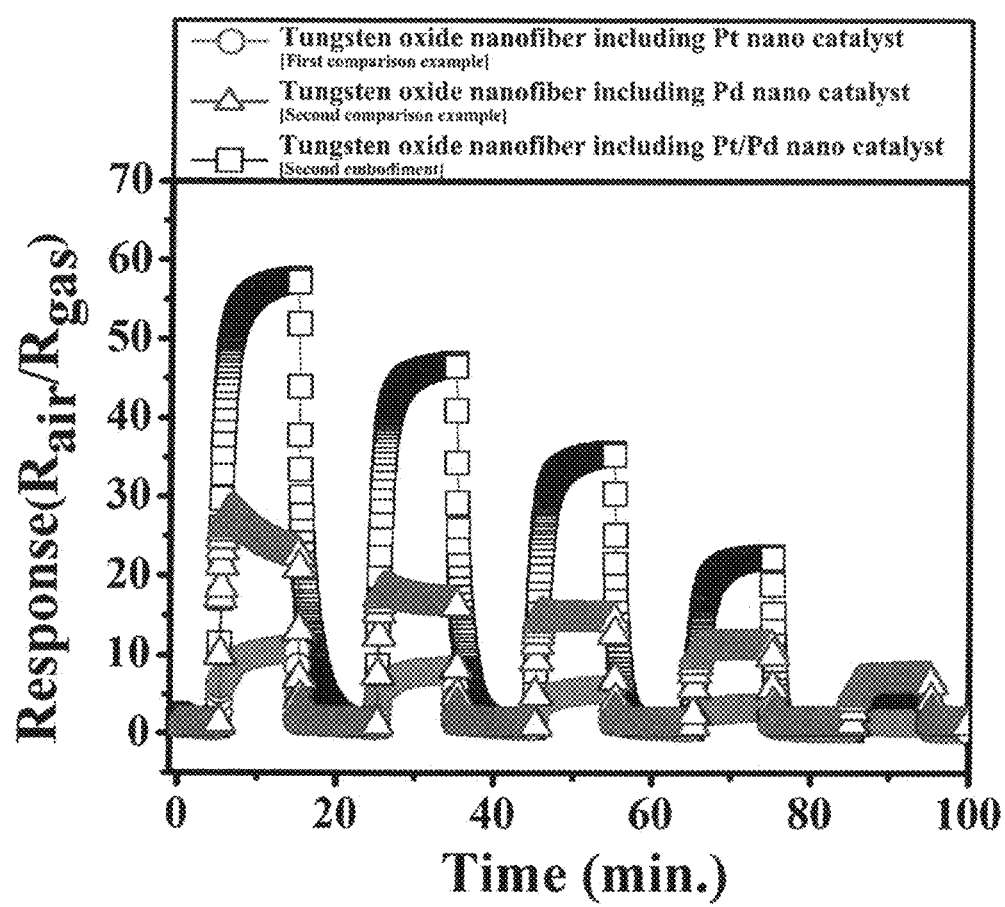
FIG. 20 is a graph showing responses of the tungsten oxide nanofibers, which include the hetero platinum/palladium nanoparticle catalyst according to an embodiment of the inventive concepts, the mono platinum nanoparticle catalyst according to the first comparison example and the mono palladium nanoparticle catalyst according to the second comparison example, respectively, to an toluene gas (1 ppm to 5 ppm) at 300 degrees Celsius.

FIG. 20 shows responses ($R_{air}/R_{gas}$) according to a time when the concentration of the toluene gas is reduced in an order of 5 ppm, 4 ppm, 3 ppm, 2 ppm, and 1 ppm at 300 degrees Celsius. Here, "$R_{air}$" denotes a resistance value of the metal oxide material when air is injected, and "$R_{gas}$" denotes a resistance value of the metal oxide material when the toluene gas is injected.

As shown in FIG. 20, the response characteristic of the sensor manufactured using the tungsten oxide nanofibers containing the hetero Pt—Pd nanoparticle catalysts is 6 times higher than that of the sensor manufactured using the tungsten oxide nanofibers containing the mono Pt nanoparticle catalysts and is 2 times higher than that of the sensor manufactured using the tungsten oxide nanofibers containing the mono Pd nanoparticle catalyst at 5 ppm.

As the results shown in FIGS. 17, 18, 19 and 20, the response characteristics of the gas sensor including the tungsten oxide nanofibers containing the hetero Pt—Pd nanoparticle catalysts with respect to acetone, ethanol, hydrogen sulfide and toluene are much higher than those of the gas sensors including the tungsten oxide nanofibers containing the mono Pt and the mono Pd. It may be verified that the hetero nanoparticle catalyst of Pt—Pd shows both the chemical sensitization effect of the mono Pt nanoparticle catalyst and the electronic sensitization effect of the mono Pd nanoparticle catalyst.

Second Experimental Example: Manufacture and Characteristic Evaluation of Gas Sensors Including Tungsten Oxide Nanofibers Including Hetero Pt—Rh Nanoparticle Catalysts, Tungsten Oxide Nanofibers Including Mono Pt Nanoparticle Catalysts, and Tungsten Oxide Nanofibers Including Mono Pd Nanoparticle Catalysts, Respectively In the second experimental example, sensors for detecting a harmful environment gas and diagnosing exhaled breath were manufactured using the tungsten oxide nanofibers containing the hetero Pt—Rh nanoparticle catalysts of the third embodiment and the tungsten oxide nanofibers containing the mono Pt nanoparticle catalysts and the mono Pd nanoparticle catalysts of the first and second comparison examples by means of the same processes and same conditions as the first experimental example. In addition, characteristics of the sensors were analyzed. However, in the second experimental example, responses of the sensors were measured at a process temperature of 350 degrees Celsius.

Figure 21:
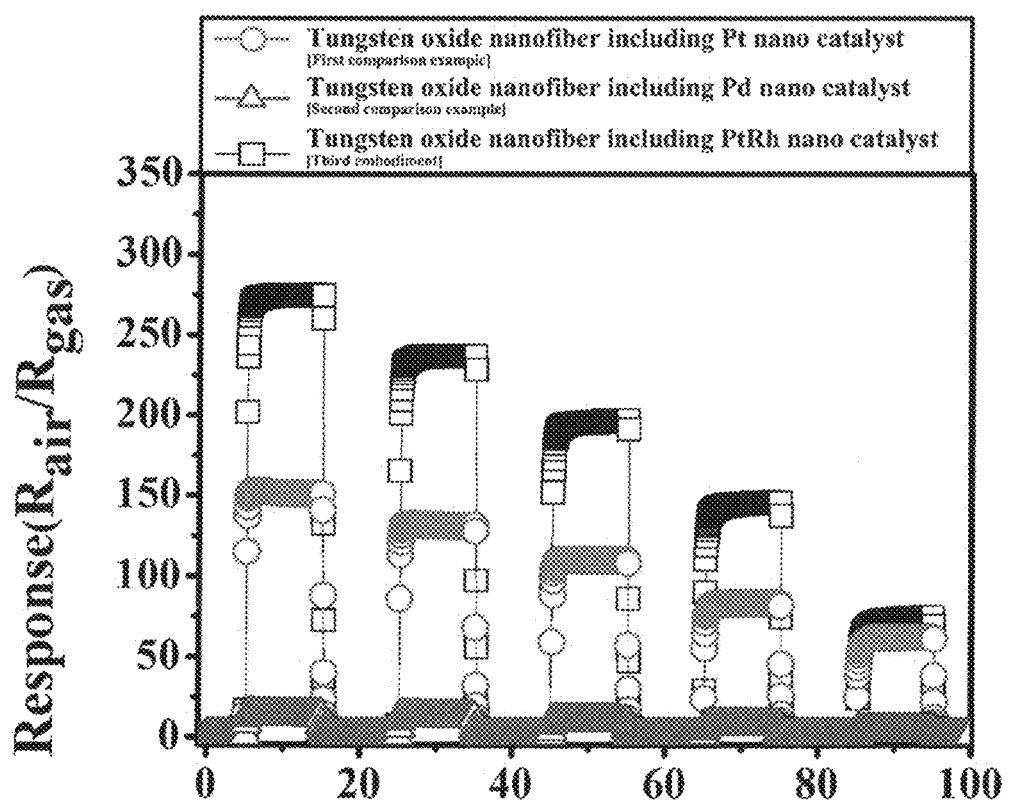
FIG. 21 is a graph showing responses of tungsten oxide nanofibers, which include the hetero platinum/rhodium nanoparticle catalyst according to an embodiment of the inventive concepts, the mono platinum nanoparticle catalyst according to the first comparison example and the mono palladium nanoparticle catalyst according to the second comparison example, respectively, to an acetone gas (1 ppm to 5 ppm) at 350 degrees Celsius.

FIG. 21 shows responses ($R_{air}/R_{gas}$) according to a time when the concentration of the acetone gas is reduced in an order of 5 ppm, 4 ppm, 3 ppm, 2 ppm, and 1 ppm at 350 degrees Celsius. Here, "$R_{air}$" denotes a resistance value of the metal oxide material when air is injected, and "$R_{gas}$" denotes a resistance value of the metal oxide material when the acetone gas is injected.

As shown in FIG. 21, the response characteristic of the sensor manufactured using the tungsten oxide nanofibers containing the hetero Pt—Rh nanoparticle catalysts is 1.8 times higher than that of the sensor manufactured using the tungsten oxide nanofibers containing the mono Pt nanoparticle catalysts and is 10 times higher than that of the sensor manufactured using the tungsten oxide nanofibers containing the mono Pd nanoparticle catalyst at 5 ppm.

Third Experimental Example: Manufacture and Characteristic Evaluation of Gas Sensors Including Tungsten Oxide Nanofibers Including Hetero Pt—Y Nanoparticle Catalysts, Tungsten Oxide Nanofibers Including Mono Pt Nanoparticle Catalysts, and Tungsten Oxide Nanofibers Including Mono Pd Nanoparticle Catalysts, Respectively In the third experimental example, sensors for detecting a harmful environment gas and diagnosing exhaled breath were manufactured using the tungsten oxide nanofibers containing the hetero Pt—Y nanoparticle catalysts of the fourth embodiment and the tungsten oxide nanofibers containing the mono Pt nanoparticle catalysts and the mono Pd nanoparticle catalysts of the first and second comparison examples by means of the same processes and same conditions as the second experimental example, and characteristics of the sensors were analyzed.

Figure 22:
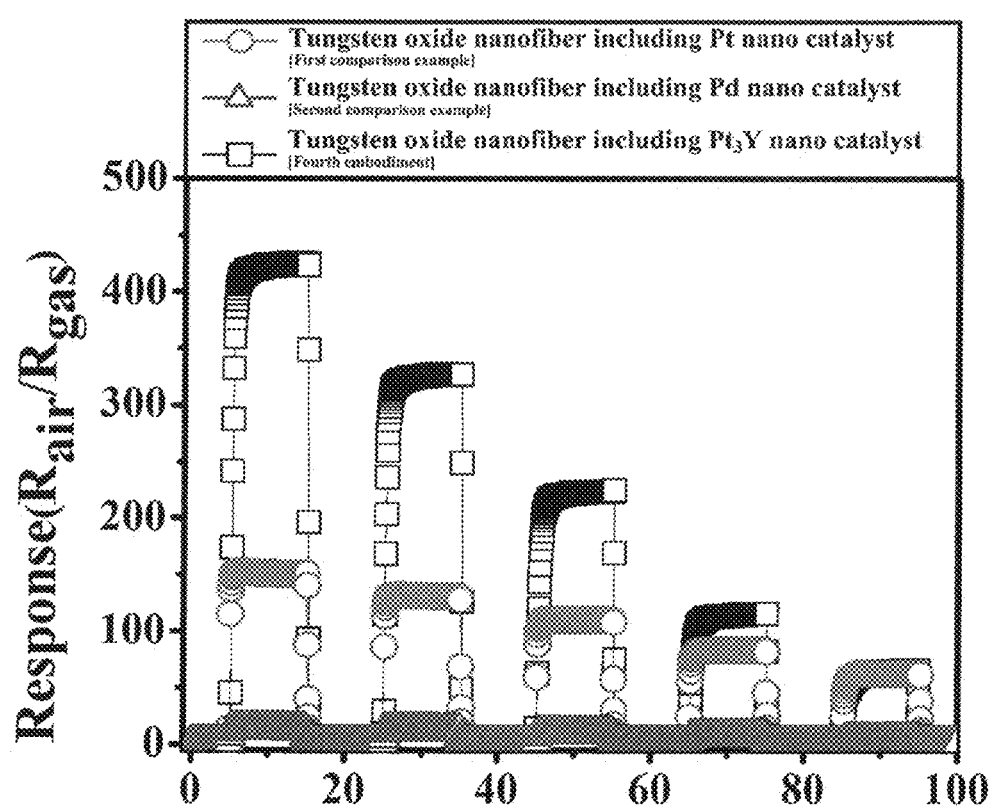
FIG. 22 is a graph showing responses of tungsten oxide nanofibers, which include the hetero platinum/yttrium nanoparticle catalyst according to an embodiment of the inventive concepts, the mono platinum nanoparticle catalyst according to the first comparison example and the mono palladium nanoparticle catalyst according to the second comparison example, respectively, to an acetone gas (1 ppm to 5 ppm) at 350 degrees Celsius.

FIG. 22 shows responses ($R_{air}/R_{gas}$) according to a time when the concentration of the acetone gas is reduced in an order of 5 ppm, 4 ppm, 3 ppm, 2 ppm, and 1 ppm at 350 degrees Celsius. Here, "$R_{air}$" denotes a resistance value of the metal oxide material when air is injected, and "$R_{gas}$" denotes a resistance value of the metal oxide material when the acetone gas is injected.

As shown in FIG. 22, the response characteristic of the sensor manufactured using the tungsten oxide nanofibers containing the hetero Pt—Y nanoparticle catalysts is 2.9 times higher than that of the sensor manufactured using the tungsten oxide nanofibers containing the mono Pt nanoparticle catalysts and is 18 time higher than that of the sensor manufactured using the tungsten oxide nanofibers containing the mono Pd nanoparticle catalyst at 5 ppm.

The experimental examples described above show the experimental results of volatile organic compound gases as an example. However, the inventive concepts are not limited thereto. The sensing materials and/or gas sensors according to the inventive concepts may have excellent gas sensing characteristics with respect to $H_2$, $NO_x$, $CO$, $SO_x$ corresponding to representative harmful environment gases. In addition, in the sensors manufactured using the tungsten oxide nanofibers containing the hetero Pt—Pd, Pt—Rh and Pt—Y nanoparticle catalysts, response sensitivity and selectivity of harmful environment gas detection and exhaled breath diagnosis may be improved by changing kinds and combinations of the hetero catalysts, by combining three or more different kinds of materials and/or by adjusting concentrations of the catalysts.

According to the inventive concepts, apo-ferritins containing hetero nanoparticle catalysts may be dispersed in the electrospinning solution to synthesize the metal oxide semiconductor nanofiber sensing material, so the hetero nanoparticle catalysts may provide the electronic and chemical sensitization effects at the same time and/or the nanofiber sensors with excellent sensitivity and selectivity may be manufactured due to new catalyst characteristics of the nano alloy catalyst. In particular, the hetero nanoparticle alloy catalysts may be converted into hetero nanoparticle catalysts having various combinations of metal-metal, metal-metal oxide and/or metal oxide-metal oxide during the thermal treatment process, so a catalyst library having excellent selectivity may be provided in manufacturing various kinds of arrays. Moreover, since the protein constituting the apo-ferritin has an excellent dispersion characteristic, the aggregation between catalyst particles may not occur to obtain excellent characteristics. Furthermore, the protein of the apo-ferritins are removed during the thermal treatment process to form the pores, and thus it is possible to realize the member for a gas sensor having excellent gas response characteristics, the gas sensor using the same, and the manufacturing method thereof.

While the inventive concepts have been described with reference to example embodiments, it will be apparent to those skilled in the art that various changes and modifications may be made without departing from the spirits and scopes of the inventive concepts. Therefore, it should be understood that the above embodiments are not limiting, but illustrative. Thus, the scopes of the inventive concepts are to be determined by the broadest permissible interpretation of the following claims and their equivalents, and shall not be restricted or limited by the foregoing description.

What is claimed is:

1. Metal oxide nanofibers comprising fine pores, wherein apo-ferritins including hetero nanoparticle catalysts are uniformly distributed in an inside and on a surface of spun metal oxide precursor/polymer complex nanofibers, and wherein proteins of the apo-ferritins are removed by a high-temperature thermal treatment process performed on the metal oxide precursor/polymer complex nanofibers such that the hetero nanoparticle catalysts are fastened to the metal oxide nanofibers;

wherein the metal oxide nanofibers comprising the fine pores are poly-crystalline nanofibers, and wherein the fine pores included in the metal oxide nanofibers are formed to have a size distribution ranging from 0.1 nm to 50 nm in a process of breaking down the proteins constituting shells of the apo-ferritins including the hetero nanoparticle catalysts by the high-temperature thermal treatment process; and wherein the metal oxide nanofibers exhibit a first grain size distribution of a metal oxide in a portion adjacent to an outer surface of the metal oxide nanofibers and exhibit a second grain size distribution of the metal oxide in a central portion of the metal oxide nanofibers, and wherein the first grain size distribution of the metal oxide is larger than the second grain size distribution of the metal oxide.

2. The metal oxide nanofibers of claim 1, wherein, after the high-temperature thermal treatment process, the hetero nanoparticle catalysts fastened in an inside and on the surface of the metal oxide nanofibers are formed of an intermetallic compound or include at least one of hetero nanoparticle catalysts expressed by metal-metal ($1M'_x$-$2M'_{1-x}$), metal-metal oxide ($1M'_x$-$2M''_yO_z$) and metal oxide-metal oxide ($1M''_yO_z$-$2M''_yO_z$) of which each has different kinds of metal components segregated from each other, where "X" is in a range of 0.01 to 99.99, "Y" is an integer equal to or greater than 1 and equal to or less than 3 and "Z" is an integer equal to or greater than 1 and equal to or less than 5.

3. The metal oxide nanofibers of claim 1, wherein the hetero nanoparticle catalysts fastened in an inside and on a surface of the metal oxide nanofibers include a hetero nanoparticle catalyst of which different kinds of metal components are formed in an alloy form expressed by $M_xM'_y$ where "M" and "M'" are the different kinds of metal components and each of "X" and "Y" is an integer ranging from 1 to 99.

4. The metal oxide nanofibers of claim 1, wherein an outer surface of the apo-ferritin is formed of the protein and an inside of the apo-ferritin has a hollow sphere-shape, and
   wherein at least one ion is included in the inside of the apo-ferritin by a substitution process, and the apo-ferritin includes a nanoparticle having a size of 0.1 nm to 8 nm through a reduction process.

5. The metal oxide nanofibers of claim 1, wherein, prior to the high-temperature thermal treatment process, a metal salt is provided into the apo-ferritins by placing the metal salt in a solution containing the apo-ferritins, the solution having a pH ranging from 1 to 5 or a pH ranging from 8.0 to 9.5.

6. The metal oxide nanofibers of claim 5, wherein the solution including the apo-ferritins has a salt ratio ranging from 0.1 mg/ml to 200 mg/ml.

7. The metal oxide nanofibers of claim 1, wherein, after the high-temperature thermal treatment process, the hetero nanoparticle catalyst included in a hollow structure of the apo-ferritin includes a metal alloy catalyst, the metal alloy catalyst being any one of a metal-metal catalyst, a metal-metal oxide catalyst, and a metal oxide-metal oxide catalyst and,
   wherein a metal of the metal-metal catalyst or the metal-metal oxide catalyst is selected from Pt and Au, and wherein a metal oxide of the metal-metal oxide or the metal oxide-metal oxide catalyst includes Ag, Fe, Ni, Ti, Y, Sn, Si, Al, Cu, Mg, Sc, V, Cr, Mn, Co, Zn, Sr, W, Ru, Rh, Ir, Ta, Sb, In, Pb, and Pd.

8. The metal oxide nanofibers of claim 1, wherein the fastened hetero nanoparticle catalysts are formed of an intermetallic compound or include at least one of hetero nanoparticle catalysts expressed by metal-metal ($1M'_x$-$2M'_{1-x}$), metal-metal oxide ($1M'_x$-$2M''_yO_z$) and metal oxide-metal oxide ($1M''_yO_z$-$2M''_yO_z$) of which each has different kinds of metal components segregated from each other,
   wherein "1M'" and "2M'" are metals selected from a group consisting of Pt and Au, and "1M''" and "2M''" are different metals, respectively,
   wherein "$M''_yO_z$" is one metal oxide selected from a group consisting of N-type semiconductor metal oxides and P-type semiconductor metal oxides, and wherein "$1M''_yO_z$" and "$2M''_yO_z$" have a metal oxide combination of N-type/N-type, N-type/P-type or P-type/P-type, and wherein "$1M''_yO_z$" and "$2M''_yO_z$" include different semiconductor metal oxides, respectively.

9. The metal oxide nanofibers of claim 1, wherein the hetero nanoparticle catalysts fastened in an inside and on a surface of the metal oxide nanofibers have a spherical, pentagonal, quadrilateral, triangular or irregular shape and sizes ranging from 0.1 nm to 8 nm.

10. The metal oxide nanofibers of claim 1, wherein the apo-ferritins including the hetero nanoparticle catalysts have a concentration ranging from 0.001 wt % to 50 wt % in the metal oxide nanofibers.

11. The metal oxide nanofibers of claim 1, wherein the metal oxide nanofibers including the fine pores have a diameter ranging from 50 nm to 10 μm and a length ranging from 1 μm to 500 μm.

12. The metal oxide nanofibers of claim 1, wherein the metal oxide nanofibers have at least one of a nanofiber shape, a nano rod shape having a shorter length than the nanofiber shape by dispersion and pulverization processes, and a nanoparticle shape pulverized from the nanofiber shape by the dispersion and pulverization processes.

13. The metal oxide nanofibers of claim 1, wherein the metal oxide nanofibers are made of a single material or complex including at least one selected from a group consisting of ZnO, $SnO_2$, $WO_3$, $Fe_2O_3$, $Fe_3O_4$, NiO, $TiO_2$, $Y_2O_3$, CuO, $In_{2O3}$, $Zn_2SnO_4$, $Co_3O_4$, PdO, $LaCoO_3$, $NiCo_2O_4$, $Ca_2Mn_3O_8$, $ZrO_2$, $Al_2O_3$, $B_2O_3$, $V_2O_5$, $Cr_3O_4$, $CeO_2$, $Pr_6O_{11}$, $Nd_2O_3$, $Sm_2O_3$, $Eu_2O_3$, $Gd_2O_3$, $Tb_4O_7$, $Dy_2O_3$, $Ho_2O_3$, $Er_2O_3$, $Yb_2O_3$, $Lu_2O_3$, $Ag_2V_4O_{11}$, $Ag_2O$, $Li_{0.3}La_{0.57}TiO_3$, $LiV_3O_8$, $RuO_2$, $IrO_2$, $MnO_2$, $InTaO_4$, ITO, IZO, $InTaO_4$, MgO, $Ga_2O_3$, $CaCu_3Ti_4O_{12}$, $Ag_3PO_4$, $BaTiO_3$, $NiTiO_3$, $SrTiO_3$, $Sr_2Nb_2O_7$, $Sr_2Ta_2O_7$, and $Ba_{0.5}Sr_{0.5}Co_{0.8}Fe_{0.2}O_{3-7}$.

14. A gas sensor comprising the metal oxide nanofibers of claim 1 as a sensing material for a gas sensor.

15. The metal oxide nanofibers of claim 8, wherein the N-type semiconductor metal oxides are selected from the group consisting of $TiO_2$, ZnO, $WO_3$, $SnO_2$, $IrO_2$, $In_2O_3$, $V_2O_3$, and $MoO_3$ and the P-type semiconductor metal oxides are selected from the group consisting of $Ag_2O$, PdO, $RuO_2$, $Rh_2O_3$, NiO, $Y_2O_3$, $Co_3O_4$, CuO, $Fe_2O_3$, $Fe_3O_4$, $V_2O_5$, and $Cr_2O_3$.

* * * * *